US010780061B2

(12) United States Patent
Cho et al.

(10) Patent No.: US 10,780,061 B2
(45) Date of Patent: Sep. 22, 2020

(54) COMPOSITION COMPRISING FARNESOL AND USE THEREOF

(71) Applicant: Daegu Gyongbuk Institute of Science and Technology, Daegu (KR)

(72) Inventors: Sungchun Cho, Hwaseongi-si (KR); Kyungho Kim, Seoul (KR); Euiseok Shin, Yongin-si (KR); Jongsun Kang, Suwon-si (KR); Jooho Shin, Seoul (KR); Juhyeon Bae, Gimcheon-si (KR); Hyeonju Jeong, Suwon-si (KR); Areum Jo, Suwon-si (KR); Sangchul Park, Seongnam-si (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 0 days.

(21) Appl. No.: 14/866,216

(22) Filed: Sep. 25, 2015

(65) Prior Publication Data

US 2016/0089340 A1 Mar. 31, 2016

(30) Foreign Application Priority Data

Sep. 26, 2014 (KR) ........................ 10-2014-0129518
Sep. 10, 2015 (KR) ........................ 10-2015-0128569

(51) Int. Cl.
*A61K 31/045* (2006.01)
*G01N 33/68* (2006.01)
*G01N 33/50* (2006.01)

(52) U.S. Cl.
CPC ....... *A61K 31/045* (2013.01); *G01N 33/5023* (2013.01); *G01N 33/6887* (2013.01)

(58) Field of Classification Search
CPC ............ A61K 31/045; G01N 33/5023; G01N 33/6887; A61P 21/00; A61P 3/04; A61P 3/08
(Continued)

(56) References Cited

U.S. PATENT DOCUMENTS 8,652,538 B2 * 2/2014 Cho ..................... A61K 36/185
424/725
2004/0202740 A1 * 10/2004 Tan ........................ A61P 39/00
424/776

(Continued)

FOREIGN PATENT DOCUMENTS

DE 196 44 422 A1 8/1998
JP 63/203694 A 8/1988
(Continued)

OTHER PUBLICATIONS

Arend Bonen (Applied Physiology, Nutrition and Metabolism, 2009, vol. 34, No. 3: pp. 307-314).*
(Continued)

*Primary Examiner* — Sabiha N Qazi
(74) *Attorney, Agent, or Firm* — Leydig, Voit & Mayer, Ltd.

(57) ABSTRACT

A method of increasing PGC-1α gene expression, decreasing PARIS gene expression, or promoting farnesylation of PARIS in a mammalian cell, the method comprising administering an effective amount of farnesol, a pharmaceutically acceptable salt thereof, or a solvate thereof to the cell; and related methods and compositions.

3 Claims, 25 Drawing Sheets

Specification includes a Sequence Listing.

(58) Field of Classification Search
USPC ...... 514/739; 435/375, 6.11, 6.12, 7.1, 7.92, 435/8; 436/501, 9
See application file for complete search history.

(56) References Cited

U.S. PATENT DOCUMENTS

| | | |
|---|---|---|
| 2006/0035849 A1 | 2/2006 | Spiegelman et al. |
| 2010/0144690 A1* | 6/2010 | Ferguson ............... A61K 31/57 514/177 |
| 2011/0112047 A1 | 5/2011 | Evans et al. |
| 2013/0017280 A1 | 1/2013 | Cho et al. |
| 2014/0271923 A1 | 9/2014 | Reid |
| 2015/0246087 A1* | 9/2015 | Hazan ..................... A61P 25/28 424/770 |

FOREIGN PATENT DOCUMENTS

| | | |
|---|---|---|
| JP | 2007-217368 A | 8/2007 |
| KR | 2011-0112072 A | 10/2011 |
| WO | WO 2007/104790 A1 | 9/2007 |

OTHER PUBLICATIONS

Joo et al. (Cancer Lett. Jan. 28, 2010: 287(2) 123), Bonen A (Appl. Physiol. Nutr. Metab. Jun. 2009; 34(3):307-14).*
Duncan et al (2008) Lipids 43: 619-627.*
Kang et al. (Ann. N.Y. Acad. Sci. ISSN 0077-8923, 892).*
Joo et al. Cancer Letter. Jan. 28, 2010; 287(2): 123, pp. 1-26, 2010).*
Ku et al. (Evidence-based complimentary and Alternate Medicine, vol. 2015, Article ID 387357, 12 pages, Hindawi printing corporatrion, 2015).*
Rigamonti et al., Arteriosclerosis, Thrombosis, and Vascular Biology. 2008; 28:1050-1059).*
Kleiner et al., PPARς Agonism Activates Fatty Acid Oxidation via PGC-1α but Does Not Increase Mitochondrial Gene Expression and Function, *The Journal of Biological Chemistry*, 284 (28): 18624-18633 (2009).
Woldt et al., Rev-erb-α modulates skeletal muscle oxidative capacity by regulating mitochondrial biogenesis and autophagy, *Nature Medicine*, 19(8): 1039-1048 (2013).
Duncan et al., "Farnesol Decreases Serum Tryglycerides in Rats: Identification of Mechanisms Including Up-Regulation of PPAR [alpha] and Down-Regulation of Fatty Acid Synthase in Hepatocytes", *Lipids*, 43(7): 619-627 (2008).
Goto et al., "Farnesol, an isoprenoid, improves metabolic abnormalities in mice via both PPARα-dependent and -independent pathways", *American Journal of Physiology: Endocrinology and Metabolism*, 301(5): E1022-E1032 (2011).
Goto et al., Various Terpenoids Derived from Herbal and Dietary Plants Function as PPAR Modulators and Regulate Carbohydrate and Lipid Metabolism, *PPAR Research*, 87(1): 8-9 (2010).
Hanai et al., "The muscle-specific ubiquitin ligase atrogin-1/MAFbx mediates statin-induced muscle toxicity", *The Journal of Clinical Investigation*, 117(12): 3940-3951 (2007).
Sandri et al., "PGC-1α protects skeletal muscle from atrophy by suppressing Fox03 action and atrophy-specific gene transcription", *Proceedings of the National Academy of Sciences*, 103(44): 16260-16265 (2006).
European Patent Office, Extended Search Report for Application No. 15186781.9, dated Jan. 29, 2016, 10 pp.
Arany et al., Transverse aortic constriction leads to accelerated heart failure in mice lacking PPAR-ɤ coactivator 1α, *Proc. Natl. Acad. Sci.*, 103(26):10086-10091 (2006).
Arany et al., HIF-independent regulation of VEGF and angiogenesis by the transcriptional coactivator PGC-1α, *Nature* 451: 1008-1012 (2008).
Arany et al., Gene expression-based screening identifies microtubule inhibitors as inducers of PGC-1α and oxidative phosphorylation, *Proc. Natl. Acad. Sci*, 105(12): 4721-4726 (2008).

Baar, et al., Adaptations of skeletal muscle to exercise: rapid increase in the transcriptional coactivator PGC-1, *FASEB Journal*, 16(14): 1879-1886 (2002).
Coll et al., Activation of Peroxisome Proliferator-Activated Receptor-ς by GW501516 Prevents Fatty Acid-Induced Nuclear Factor-κB Activation and Insulin Resistance in Skeletal Muscle Cells, *Endocrinology*, 151(4): 1560-1569 (2010).
Egawa et al., AICAR-induced activation of AMPK negatively regulates myotube hypertrophy through the HSP72-mediated pathway in $C_2C_{12}$ skeletal muscle cells, *Am. J. Physiol. Endocrinol. Metab.*, 306: E344-E354 (2014).
Handschin et al., PGC-1α regulates the neuromuscular junction program and ameliorates Duchenne muscular dystrophy, *Genes & Development*, 21:770-783 (2007).
Norrbom et al., PGC-1α mRNA expression is influenced by metabolic perturbation in exercising human skeletal muscle, *J Appl Physiol.*, 96:189-194 (2004).
Rangwala et al., Estrogen-related Receptor ɤ Is a Key Regulator of Muscle Mitochondrial Activity and Oxidative Capacity, *Journal of Biological Chemistry*, 285(29): 22619-22629 (2010).
Tanaka et al., Activation of peroxisome proliferator-activated receptor ς induces fatty acid β-oxidation in skeletal muscle and attenuates metabolic syndrome, *Proc. Natl. Acad. Sci.*, 100(26): 15924-15929 (2003).
Wang et al., An ERR β/ɤ agonist modulates GRα expression, and glucocorticoid responsive gene expression in skeletal muscle cells, *Molecular and Cellular Endocrinology*, 315: 146-152 (2010).
Pablo J. Fernandez-Marcos et al., "Regulation of PGC-1α, a nodal regulator of mitochondrial biogenesis," *Am J Clin Natr*, 93, pp. 884S-890S (2011).
European Patent Office, Extended Search Report for Application No. 15186781.9, dated May 24, 2016, 15 pp.
Tyagi et al. "The peroxisome proliferator-activated receptor: A Family of nuclear receptors role in various diseases," *J. Adv Pharm Technol. Res*, 2(4) 236-240 (2011).
GeneCards Databas Entry for ID GC04M023755 (PPARGC1A), Genecards Human Genome Database, Weizmann Institute of Science (Israel), downloaded on Aug. 31, 2018.
GeneCards Databas Entry for ID GC22P046150 (PPARA), Genecards Human Genome Database, Weizmann Institute of Science (Israel), downloaded on Aug. 31, 2018.
Arany et al., Transcriptional coactivator PGC-1α alpha controls the energy state and contractile function of cardiac muscle, *Cell Metabolism*, 1:259-271 (2005).
Arany et al., Transverse aortic constriction leads to accelerated heart failure in mice lacking PPAR-ɤ coactivator 1α, *Proc. Natl. Acad. Sci.*, 103(26):10086-10091 (2006).
Arany et al., HIF-independent regulation of VEGF and angiogensis by the transcriptional coactivator PGC-1α, *Nature* 451: 1008-1012 (2008).
Arany et al., Gene expression-based screening identifies microtubule inhibitors as inducers of PGC-1α and oxidavtive phosphorylation, *Proc. Natl. Acad. Sc*, 105(12):4721-4726 (2008).
Baar, et al., Adaptations of skeletal muscle to exercise: rapid increase in the transcriptional coactivator PGC-1, *FASEB Journal*, 16(4):1879-1886 (2002).
Coll et al., Activation of Peroxisome Proliferator-Activated Receptor-δ by GW201516 Prevents Fatty Acid-Induced Nuclear Factor-xB Activation and Insulin Resistance in Skeletal Muscle Cells, *Endocrinology*, 151(4): 1560-1569 (2010).
Cluberton et al., Effect of carbohydrate ingestion on exercise-induced alterations in metabolic gene expression, *J. Appl. Physiol.* 99:1359-1363 (2005).
Egawa et al., AICAR-induced actiation of AMPK negatively regulates motube hypertrophy through the HSP72-mediated pathway in $C_2C_{12}$ skeletal muscle cells, *Am. J. Physicol. Endocrinol. Metab.*, 306: E344-E354 (2014).
Forman et al., Identification of a Nuclear Receptor That Is Activated by Farnesol Metabolites, *Cell*, 81(5):687-693 (1995).
Handschin et al., PGC-1α regulates the neuromascular junction program and ameliorates Duchenne muscular dystrophy, *Genes & Development*, 21:770-783 (2007).

(56) References Cited

OTHER PUBLICATIONS

Herzig et al., Creb regulates hepatic gluconeogenesis through the coactivator PGC-1, *Nature* 413:179-183 (2001).
Hurst et al., Amp-activated protein kinase kinase activity and phosphorylation of AMP-activated protein kinase in contracting muscle of sedentary and endurance-trained rats, *Am. J. Physiol. Endocrinol. Metab.*, 289: E710-E715 (2005).
Lin et al., Transcriptional co-activator PGC-1α drives the formation of slow-twitch muscle fibres, *Nature*, 418:797-801 (2002).
Lin et al., Defects in Adaptive Energy Metabolism with CNS-linked hyperactivity in *PGC*-1α Null Mice, *Cell* 119:121-135 (2004).
Norrbom et al., PGC-1α mRNA expression is influenced by metabolic perturbation in exercising human skeletal muscle, *J App Physiol.*, 96:189-194 (2004).
Rangwala et al., Estrogen-related Receptor γ Is a Key Regulator of Muscle Mitochondrial Activity and Oxidative Capacity, *Journal of Biological Chemistry*, 285(29): 22619-22629 (2010).
Sandri et al., PGC-1α protects skeletal muscle from atrophy by suppressing FoxO3 action and atrophy-specific gene transcription, *Proc. Natl. Acad. Sci.*, 103(44):16260-16265 (2006).
Solt et al., Regulation of circadian behavior and metabolism by synthetic REV-ERB agonists, *Nature*; 485: 62-68 (2012).
Tanaka et al., Activation of peroxisome proliferator-activated receptor ζ induces fatty acid ⊖-oxidation in skeletal muscle and attenuates metabolic syndrome, *Proc. Natl. Acad. Sci.*, 100(26): 15924-15929 (2003).
Taylor et al., Endurance training increases skeletal muscle LKB1 and PGC-1α protein abundance: effects of time and intensity, *Am. J. Physiol. Endocrinol. Metab.*, 289: E960-E968 (2005).
Wang et al., an ERR β/γ agonist modulates GRα expression, and glucocorticoid responsive gene expression in skeletal muscle cells, *Molecular and Cellular Endocrinology*, 315: 146-152 (2010).
Yoon et al., Control of hepatic gluconeogenesis through the transcriptional coactivator PGC-1, *Nature*, 413:131-138 (2001).
Zhang et al., Novel small-molecule PGC-1α Transcriptional Regulator With Beneficial Effects on Diabetic *db/db*Mice, *Diabetes*, 62(4):1297-1307 (2013).

\* cited by examiner (A)  (B)

(A)     (B)

(A)　　　　　　　　　　　　(B)

SEQUENCE LISTING

<160> NUMBER OF SEQ ID NOS: 13

<210> SEQ ID NO 1
<211> LENGTH: 21
<212> TYPE: DNA
<213> ORGANISM: Artificial Sequence
<220> FEATURE:
<223> OTHER INFORMATION: Synthetic Col1a1 F primer

<400> SEQUENCE: 1
tcatcgtggc ttctcctggt c                                              21

<210> SEQ ID NO 2
<211> LENGTH: 20
<212> TYPE: DNA
<213> ORGANISM: Artificial Sequence
<220> FEATURE:
<223> OTHER INFORMATION: Synthetic Col1a1 R primer

<400> SEQUENCE: 2
gaccgttgag tccgtctttg                                                20

<210> SEQ ID NO 3
<211> LENGTH: 21
<212> TYPE: DNA
<213> ORGANISM: Artificial Sequence
<220> FEATURE:
<223> OTHER INFORMATION: Synthetic Cola3 F primer

<400> SEQUENCE: 3
acgtaagcac tggtggacag a                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic Cola3 R primer

<400> SEQUENCE: 4
gagggccata gctgaactga                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic TGFb F primer

<400> SEQUENCE: 5
tcgacatgga gctggtgaaa                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic TGFb R primer

<400> SEQUENCE: 6
ctggcgagcc ttagtttgga                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic Timp2 F primer

<400> SEQUENCE: 7
ggaatgacat ctatggcaac c                                              21

<210> SEQ ID NO 8
<211> LENGTH: 21

```
<212> TYPE: DNA
<213> ORGANISM: Artificial Sequence
<220> FEATURE:
<223> OTHER INFORMATION: Synthetic Timp2 R primer

<400> SEQUENCE: 8
ggccgtgtag ataaactcga t                                             21

<210> SEQ ID NO 9
<211> LENGTH: 3706
<212> TYPE: DNA
<213> ORGANISM: Homo sapiens

<400> SEQUENCE: 9
```

| | | | | |
|---|---|---|---|---|
| gcgactgcgg | gcggcgcggc | gcaggggcag | ccagcgagga | gcggcggcag | aggaaaggcc | 60 |
| aggcaggcgc | cgcctgcgga | gagcaccggg | cggccgggcc | tgcgtggtgc | cgcgcgcggc | 120 |
| ggcggcgacg | acgacttcct | ccgggccggg | cgggacagcg | cagggccatg | gccgaggcgg | 180 |
| tcgcggctcc | gatttctccg | tggacgatgg | cagccacgat | tcaggccatg | gagaggaaga | 240 |
| ttgaatcgca | ggctgctcgc | ctgctttccc | tagaaggtcg | aaccgggatg | gccgagaaga | 300 |
| agctggctga | ttgcgagaag | acagccgtgg | agttcgggaa | ccagctggag | ggcaagtggg | 360 |
| ccgtgctggg | gaccctgctg | caggagtacg | ggctgctgca | gaggcggctg | gagaacgtgg | 420 |
| agaacctgct | gcgcaacagg | aacttctgga | tcctgcggct | gccccccggc | agcaagggg | 480 |
| agtcccctaa | ggagtggggc | aagctggagg | actggcagaa | ggagctctac | aagcacgtga | 540 |
| tgaggggcaa | ctacgagacg | ctggtctccc | tggactacgc | catctccaag | cccgaggtcc | 600 |
| tctcccagat | tgaacaaggg | aaggagccct | gcaactggcg | ccgcctggc | cccaagattc | 660 |
| cagatgttcc | tgtggacccc | agtccaggct | cggggccccc | agttcccgcc | ccagacctct | 720 |
| tgatgcagat | caagcaggag | ggtgagctcc | agctccagga | gcagcaggcc | ctgggcgtgg | 780 |
| aggcgtgggc | agccgggcag | ccagatattg | ggaggagcc | ctggggcctc | agccagctgg | 840 |
| attccggagc | aggagacatc | tccacggatg | ccacctctgg | tgtccattcc | aacttttcca | 900 |
| ccaccatccc | gcccacctcc | tggcaaacg | atctccctcc | ccaccatccc | tcttcagcat | 960 |
| gctcggacgg | gaccctgaag | ctcaacacag | cagcctccac | ggaagatgta | aaaattgtaa | 1020 |
| taaaaacaga | agtccaggaa | gaggaggtgg | tggccacacc | cgtacatcct | actgacctag | 1080 |
| aggctcacgg | gaccctgttt | ggaccaggcc | aagccacacg | gttcttccct | agtcctgccc | 1140 |
| aggaaggagc | ctgggaaagc | cagggcagct | ccttccccag | ccaggaccct | gtgctggggc | 1200 |
| tgcgagagcc | cgcccggcct | gagagggaca | tgggtgagct | cagtcctgct | gtggcccagg | 1260 |
| aggagacccc | tcctggggac | tggctcttcg | gaggggtccg | gtggggctgg | aatttccggt | 1320 |
| gtaaaccgcc | agtgggcctg | aacccgagga | cgggccccga | ggggcttcct | tactcctccc | 1380 |
| cggacaacgg | agaggccatc | ttggacccca | gccaggcccc | aaggccattc | aacgaaccct | 1440 |
| gtaaataccc | tggccggacc | aaaggctttg | gccacaagcc | agggctgaag | aagcaccccg | 1500 |
| cggcgccccc | cggggggcgg | cccttcacct | gcgccacgtg | tgggaagagc | ttccagctgc | 1560 |
| aagtcagcct | gagcgcgcac | cagcgcagct | gtgggggcgcc | cgacgggtcg | ggcccgggca | 1620 |
| caggcggtgg | cggcagcggc | agtgcggcg | gcggtggcgg | cagcggtggg | ggcagcgcac | 1680 |
| gggatggcag | cgcccttcgg | tgtggggagt | gcggccgttg | cttcacgcgc | cccgcgcacc | 1740 |
| tcatccgcca | tcgcatgctg | cacaccggcg | agcggccctt | cccctgcacc | gagtgtgaga | 1800 |
| agcgcttcac | cgaacgctcc | aagctcatcg | accactaccg | aacgcacacg | ggcgtgcggc | 1860 |

-continued

```
ccttcacctg caccgtctgc ggcaaaagct tcatccgcaa ggaccacctc cgcaagcacc      1920
agcgcaacca tgcagcgggc gccaagaccc cggcccgagg ccagccactc ccgacgccgc      1980
ccgcacctcc tgatcccttc aagagccccg cctccaaagg acctttggcc tccacagacc      2040
ttgtgaccga ctggacttgt ggcctcagcg tcctgggacc caccgatggc ggggacatgt      2100
gagcgcctcc agcccatag cccctgccgg ccgcacgtgt aaaaagcccc gtgtgcaggc       2160
agcagggcgg cgtggaagct tcaggcagac gcgggacggg gagaaccaaa tgtccaagtt      2220
gctgaactga tgatcactgg agaaagagaa actatccacc aggacagctg ccacctctaa      2280
accaagtaga attctctgtg aaatgggagc gccgtagaat tttaagtaat ttaattgcaa      2340
acctgttttg ttttttgttt tttgttttt tttaattctt gaggaaaaag ctggaaaata      2400
gtaatagggc tatttaaatt ttgtaggtac ttttggtttt cagggcgtgc atttctgtca      2460
ctatctcact gagtctgata gtgtgttgga aggttggcca gttggggacc cctggcccac      2520
tgactcctgg ggatggggtc ctgtgtgtgc ccctgctctg cccagttggg ctgagtgggc      2580
ctagcgcacc aagcccctgg gcagtgaggg ccattgggtc ccttggagca cacctcagtg      2640
cagcaggaag gaccccctccg ggagtagcgg ttgcatttcc cagcttgcct ctcctgaaaa      2700 ggcccccccaa aagtgctggc cccaactttt ctctattttg ggccatctgt ggtacccgtc      2760
ccaagggcac ttggtggtgt cccctagtgt gtgactccct ggcctcataa ggacgagttg      2820
tctgaaatcc cagcgttagg tctggggaga tggagaagct gaaactgggg agctgcacca      2880
caaacgtcta gctctcagca gagctggagg caaagcctgg ccgcccaccc caacctgggg      2940
ctgcctccca ctccgtgaga tgcttctgtc tcctgttcac tttgtgtggt agtttcttat      3000
tttcaaaatg catctcattt gatcattact gtgaccttgg gaagcagcag gacagggatt      3060
tctttttaga ggtgcaaact gctcagaggg gacacacctc agcctctcac tgtgggtaca      3120
cgtggcgtgc catgagtggg gaagagcaac aggcgagatg cctcattcta ctggaacatc      3180
actgtgggtg aacagagatt tccaggtttt ccctcttaaa atatttgtcc cacaccgaca      3240
agagtccagt caccaggcct caaaggaact tctgcttgta gcagccgcct ccctgtgcc       3300 ccagcctcct taatgtgtgc actctcagag ggcacagctc gcgaggctgg gtttgggggc      3360
caagtggctt gttcattcca gcatctaaca tcataaaggt gggcccagat tcttgattc       3420 gaccacagtg ctgttcctac cacacaaata tccattcctg ttttgttgaa gcagccactg      3480
gtcctcttgt ttccctgca gacggaggga cctggcagtg cccattcatt cagccccctc       3540
atgcatactt ttattaggcg atagactagt taagaaaatt gtttctatgt actgtatatt      3600
ttgtacctgt ttacacttct aatattgata taactgatat tttgaaaaat aagagaaaac      3660
atcctgttaa ataaaacct aaccagcacc aaaaaaaaaa aaaaaa                     3706
```

<210> SEQ ID NO 10
<211> LENGTH: 652
<212> TYPE: PRT
<213> ORGANISM: Mus musculus

<400> SEQUENCE: 10

```
Met Ala Glu Ala Ala Ala Ala Pro Ile Ser Pro Trp Thr Met Ala Ala
1               5                   10                  15

Thr Ile Gln Ala Met Glu Arg Lys Ile Glu Ser Gln Ala Ala Arg Leu
            20                  25                  30

Leu Ser Leu Glu Gly Arg Thr Gly Met Ala Glu Lys Lys Leu Ala Asp
        35                  40                  45
```

-continued

```
Cys Glu Lys Thr Ala Val Glu Phe Ser Asn Gln Leu Glu Gly Lys Trp
 50                  55                  60
Ala Val Leu Gly Thr Leu Leu Gln Glu Tyr Gly Leu Leu Gln Arg Arg
 65                  70                  75                  80
Leu Glu Asn Val Glu Asn Leu Leu Arg Asn Arg Asn Phe Trp Ile Leu
                 85                  90                  95
Arg Leu Pro Pro Gly Ser Lys Gly Glu Val Pro Lys Glu Trp Gly Lys
            100                 105                 110
Leu Glu Asp Trp Gln Lys Glu Leu Tyr Lys His Val Met Arg Gly Asn
            115                 120                 125
Tyr Glu Thr Leu Val Ser Leu Asp Tyr Ala Ile Ser Lys Pro Glu Val
            130                 135                 140
Leu Ser Gln Ile Glu Gln Gly Lys Glu Pro Cys Thr Trp Arg Arg Thr
145                 150                 155                 160
Gly Pro Lys Val Pro Glu Val Pro Val Asp Pro Ser Pro Gly Ser Gly
                165                 170                 175
Ala Pro Val Pro Ala Pro Asp Leu Leu Met Gln Ile Lys Gln Glu Gly
            180                 185                 190
Glu Leu Gln Leu Gln Glu Gln Gln Ala Leu Gly Val Glu Ala Trp Ala
            195                 200                 205
Ala Gly Gln Pro Asp Ile Gly Glu Glu Pro Trp Gly Leu Ser Gln Leu
            210                 215                 220
Asp Ser Gly Ala Gly Asp Ile Ser Thr Asp Ala Thr Ser Gly Val His
225                 230                 235                 240
Ser Asn Phe Ser Thr Thr Ile Pro Pro Thr Ser Trp Gln Ala Asp Leu
                245                 250                 255
Pro Pro His His Pro Ser Ser Ala Cys Ser Asp Gly Thr Leu Lys Leu
            260                 265                 270
Asn Thr Ala Ala Ser Thr Glu Ala Asp Val Lys Ile Val Ile Lys Thr
            275                 280                 285
Glu Val Gln Glu Glu Val Val Ala Thr Pro Val His Pro Thr Asp
            290                 295                 300
Leu Glu Ala His Gly Thr Leu Phe Ala Pro Gly Gln Ala Thr Arg Phe
305                 310                 315                 320
Phe Pro Ser Pro Val Gln Glu Gly Ala Trp Glu Ser Gln Gly Ser Ser
                325                 330                 335
Phe Pro Ser Gln Asp Pro Val Leu Gly Leu Arg Glu Pro Thr Arg Pro
            340                 345                 350
Glu Arg Asp Ile Gly Glu Leu Ser Pro Ala Ile Ala Gln Glu Glu Ala
            355                 360                 365
Pro Ala Gly Asp Trp Leu Phe Gly Gly Val Arg Trp Gly Trp Asn Phe
            370                 375                 380
Arg Cys Lys Pro Pro Val Gly Leu Asn Pro Arg Thr Val Pro Glu Gly
385                 390                 395                 400
Leu Pro Phe Ser Ser Pro Asp Asn Gly Glu Ala Ile Leu Asp Pro Ser
                405                 410                 415
Gln Ala Pro Arg Pro Phe Asn Asp Pro Cys Lys Tyr Pro Gly Arg Thr
            420                 425                 430
Lys Gly Phe Gly His Lys Pro Gly Leu Lys Lys His Pro Ala Ala Pro
            435                 440                 445
Pro Gly Gly Arg Pro Phe Thr Cys Ala Thr Cys Gly Lys Ser Phe Gln
            450                 455                 460
Leu Gln Val Ser Leu Ser Ala His Gln Arg Ser Cys Gly Leu Ser Asp
```

```
            465                 470                 475                 480
        Gly Ala Ala Thr Gly Ala Ala Ser Thr Thr Thr Gly Gly Gly Gly Gly
                        485                 490                 495

Gly Ser Gly Gly Gly Gly Ser Ser Gly Gly Ser Ser Ala Arg
                        500                 505                 510

Asp Ser Ser Ala Leu Arg Cys Gly Glu Cys Gly Arg Cys Phe Thr Arg
                        515                 520                 525

Pro Ala His Leu Ile Arg His Arg Met Leu His Thr Gly Glu Arg Pro
                    530                 535                 540

Phe Pro Cys Thr Glu Cys Glu Lys Arg Phe Thr Glu Arg Ser Lys Leu
        545                 550                 555                 560

Ile Asp His Tyr Arg Thr His Thr Gly Val Arg Pro Phe Thr Cys Thr
                            565                 570                 575

Val Cys Gly Lys Ser Phe Ile Arg Lys Asp His Leu Arg Lys His Gln
                        580                 585                 590

Arg Asn His Pro Ala Val Ala Lys Ala Pro Ala His Gly Gln Pro Leu
                    595                 600                 605

Pro Pro Leu Pro Ala Pro Pro Asp Pro Phe Lys Ser Pro Ala Ala Lys
        610                 615                 620

Gly Pro Met Ala Ser Thr Asp Leu Val Thr Asp Trp Thr Cys Gly Leu
        625                 630                 635                 640

Ser Val Leu Gly Pro Ser Asp Gly Gly Asp Leu
                        645                 650

<210> SEQ ID NO 11
<211> LENGTH: 644
<212> TYPE: PRT
<213> ORGANISM: Homo sapiens

<400> SEQUENCE: 11

Met Ala Glu Ala Val Ala Ala Pro Ile Ser Pro Trp Thr Met Ala Ala
1               5                   10                  15

Thr Ile Gln Ala Met Glu Arg Lys Ile Glu Ser Gln Ala Ala Arg Leu
            20                  25                  30

Leu Ser Leu Glu Gly Arg Thr Gly Met Ala Glu Lys Lys Leu Ala Asp
        35                  40                  45

Cys Glu Lys Thr Ala Val Glu Phe Gly Asn Gln Leu Glu Gly Lys Trp
50                  55                  60

Ala Val Leu Gly Thr Leu Leu Gln Glu Tyr Gly Leu Leu Gln Arg Arg
65                  70                  75                  80

Leu Glu Asn Val Glu Asn Leu Arg Asn Arg Asn Phe Trp Ile Leu
                85                  90                  95

Arg Leu Pro Pro Gly Ser Lys Gly Glu Ser Pro Lys Trp Gly Lys
                100                 105                 110

Leu Glu Asp Trp Gln Lys Glu Leu Tyr Lys His Val Met Arg Gly Asn
            115                 120                 125

Tyr Glu Thr Leu Val Ser Leu Asp Tyr Ala Ile Ser Lys Pro Glu Val
        130                 135                 140

Leu Ser Gln Ile Glu Gln Gly Lys Glu Pro Cys Asn Trp Arg Arg Pro
145                 150                 155                 160

Gly Pro Lys Ile Pro Asp Val Pro Val Asp Pro Ser Pro Gly Ser Gly
                165                 170                 175

Pro Pro Val Pro Ala Pro Asp Leu Leu Met Gln Ile Lys Gln Glu Gly
            180                 185                 190
```

-continued

```
Glu Leu Gln Leu Gln Glu Gln Ala Leu Gly Val Glu Ala Trp Ala
        195                 200                 205
Ala Gly Gln Pro Asp Ile Gly Glu Glu Pro Trp Gly Leu Ser Gln Leu
    210                 215                 220
Asp Ser Gly Ala Gly Asp Ile Ser Thr Asp Ala Thr Ser Gly Val His
225                 230                 235                 240
Ser Asn Phe Ser Thr Thr Ile Pro Pro Thr Ser Trp Gln Thr Asp Leu
                245                 250                 255
Pro Pro His His Pro Ser Ser Ala Cys Ser Asp Gly Thr Leu Lys Leu
            260                 265                 270
Asn Thr Ala Ala Ser Thr Glu Asp Val Lys Ile Val Lys Thr Glu
        275                 280                 285
Val Gln Glu Glu Glu Val Val Ala Thr Pro Val His Pro Thr Asp Leu
    290                 295                 300
Glu Ala His Gly Thr Leu Phe Gly Pro Gly Gln Ala Thr Arg Phe Phe
305                 310                 315                 320
Pro Ser Pro Ala Gln Glu Gly Ala Trp Glu Ser Gln Gly Ser Ser Phe
                325                 330                 335
Pro Ser Gln Asp Pro Val Leu Gly Leu Arg Glu Pro Ala Arg Pro Glu
            340                 345                 350
Arg Asp Met Gly Glu Leu Ser Pro Ala Val Ala Gln Glu Glu Thr Pro
        355                 360                 365
Pro Gly Asp Trp Leu Phe Gly Gly Val Arg Trp Gly Trp Asn Phe Arg
    370                 375                 380
Cys Lys Pro Pro Val Gly Leu Asn Pro Arg Thr Gly Pro Glu Gly Leu
385                 390                 395                 400
Pro Tyr Ser Ser Pro Asp Asn Gly Glu Ala Ile Leu Asp Pro Ser Gln
                405                 410                 415
Ala Pro Arg Pro Phe Asn Glu Pro Cys Lys Tyr Pro Gly Arg Thr Lys
            420                 425                 430
Gly Phe Gly His Lys Pro Gly Leu Lys Lys His Pro Ala Ala Pro Pro
        435                 440                 445
Gly Gly Arg Pro Phe Thr Cys Ala Thr Cys Gly Lys Ser Phe Gln Leu
    450                 455                 460
Gln Val Ser Leu Ser Ala His Gln Arg Ser Cys Gly Ala Pro Asp Gly
465                 470                 475                 480
Ser Gly Pro Gly Thr Gly Gly Gly Ser Gly Gly Gly Gly
                485                 490                 495
Gly Gly Ser Gly Gly Ser Ala Arg Asp Gly Ser Ala Leu Arg Cys
            500                 505                 510
Gly Glu Cys Gly Arg Cys Phe Thr Arg Pro Ala His Leu Ile Arg His
        515                 520                 525
Arg Met Leu His Thr Gly Glu Arg Pro Phe Pro Cys Thr Glu Cys Glu
    530                 535                 540
Lys Arg Phe Thr Glu Arg Ser Lys Leu Ile Asp His Tyr Arg Thr His
545                 550                 555                 560
Thr Gly Val Arg Pro Phe Thr Cys Thr Val Cys Gly Lys Ser Phe Ile
                565                 570                 575
Arg Lys Asp His Leu Arg Lys His Gln Arg Asn His Ala Ala Gly Ala
            580                 585                 590
Lys Thr Pro Ala Arg Gly Gln Pro Leu Pro Thr Pro Ala Pro Pro
        595                 600                 605
Asp Pro Phe Lys Ser Pro Ala Ser Lys Gly Pro Leu Ala Ser Thr Asp
```

```
             610                 615                 620
Leu Val Thr Asp Trp Thr Cys Gly Leu Ser Val Leu Gly Pro Thr Asp
625                 630                 635                 640

Gly Gly Asp Met

<210> SEQ ID NO 12
<211> LENGTH: 26
<212> TYPE: DNA
<213> ORGANISM: Artificial Sequence
<220> FEATURE:
<223> OTHER INFORMATION: Synthetic Sequencing F primer

<400> SEQUENCE: 12
gaccgactgg actagtggcc tcagcg                                         26

<210> SEQ ID NO 13
<211> LENGTH: 26
<212> TYPE: DNA
<213> ORGANISM: Artificial Sequence
<220> FEATURE:
<223> OTHER INFORMATION: Synthetic Sequencing R primer

<400> SEQUENCE: 13
cgctgaggcc actagtccag tcggtc                                         26
```

COMPOSITION COMPRISING FARNESOL AND USE THEREOF

CROSS-REFERENCE TO RELATED APPLICATIONS

This application claims the benefit of Korean Patent Application No. 10-2014-0129518, filed on Sep. 26, 2014, and Korean Patent Application No. 10-2015-0128569, filed on Sep. 10, 2015, in the Korean Intellectual Property Office, the entire disclosures of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 17,691 Byte ASCII (Text) file named "721894_ST25.TXT," created on Sep. 25, 2015.

BACKGROUND

1. Field

The present disclosure relates to a composition including farnesol and use thereof.

2. Description of the Related Art

PGC-1α (peroxisome proliferator-activated receptor gamma coactivator-1 alpha) is known to bind to PPAR-gamma (peroxisome proliferator-activated receptor-gamma) and many different nuclear receptors to be involved in the regulation of genes related to energy metabolism. PGC-1α expression is increased in muscle cells by exercise to promote mitochondrial biogenesis and to increase proportion of oxidative muscle fibers in skeletal muscles.

Farnesol is a natural compound found in many fruits and aromatic plants. Farnesol has been known to have various biological functions such as signal transduction, quorum sensing, cell proliferation, cell death, etc., and it has been also developed as an anticancer agent. However, the previous studies have never reported effects of farnesol on PGC-1α.

SUMMARY

Provided herein is a composition for increasing PGC-1α gene expression, decreasing PARIS gene expression, or promoting farnesylation of PARIS in a mammalian cell, the composition including farnesol, a pharmaceutically acceptable salt thereof, or a solvate thereof as an active ingredient.

Also provided is a composition for converting muscle type II into muscle type I or increasing muscle type I, the composition including farnesol, a pharmaceutically acceptable salt thereof, or a solvate thereof as an active ingredient.

Another aspect of the disclosure provides a composition for strengthening muscles or increasing exercise performance in a mammal, the composition including farnesol, a pharmaceutically acceptable salt thereof, or a solvate thereof as an active ingredient.

Still another aspect of the disclosure provides a composition for reducing fat, inhibiting fat accumulation, or reducing blood glucose in the body of a mammal, the composition including farnesol, a pharmaceutically acceptable salt thereof, or a solvate thereof as an active ingredient.

Further provided is a composition for treating muscle fibrosis of a mammal, the composition including farnesol, a pharmaceutically acceptable salt thereof, or a solvate thereof as an active ingredient.

A method of increasing PGC-1α gene expression, decreasing PARIS gene expression, or promoting farnesylation of PARIS in a mammalian cell, is provided herein, the method including administering an effective amount of farnesol, a pharmaceutically acceptable salt thereof, or a solvate thereof to the cell.

Also provided is a method of converting muscle type II into muscle type I in a subject, or increasing muscle type I in a subject, the method including administering an effective amount of farnesol, a pharmaceutically acceptable salt thereof, or a solvate thereof to the subject.

In another aspect, the disclosure provides a method of strengthening muscles or increasing exercise performance in a subject, the method including administering an effective amount of farnesol, a pharmaceutically acceptable salt thereof, or a solvate thereof to the subject.

Further provided is a method of reducing fat, inhibiting fat accumulation, or reducing blood glucose in the body of a subject, the method including administering an effective amount of farnesol, a pharmaceutically acceptable salt thereof, or a solvate to the subject.

Also provided is a method of treating muscle fibrosis of a subject, the method including administering an effective amount of farnesol, a pharmaceutically acceptable salt thereof, or a solvate to the subject.

Still another aspect provides a method of screening for a compound capable of reducing PGC-1α expression in a mammalian cell, the method including contacting a candidate compound with the mammalian cell; and measuring an expression level of PARIS gene or a farnesylation level of PARIS protein in the cell.

In another aspect, there is provided a method of determining an exercise performance in a mammalian subject, the method comprising: measuring an expression level of PARIS gene or a farnesylation level of PARIS protein in a cell of the mammalian subject; and comparing the obtained expression level of PARIS gene or the obtained farnesylation level of PARIS protein with a predetermined value.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1A:
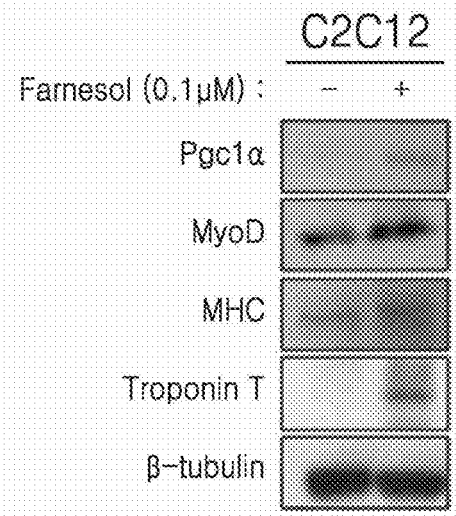
FIG. 1A shows expression changes of PGC-1α and muscle differentiation markers by treatment of myoblast with farnesol.

Provided is a composition for increasing PGC-1α gene expression, decreasing PARIS gene expression, or promoting farnesylation of PARIS in a mammalian cell, the composition including farnesol, a pharmaceutically acceptable salt thereof, or a solvate thereof as an active ingredient.

Also provided is a composition for converting muscle type II into muscle type I or increasing muscle type I, the composition including farnesol, a pharmaceutically acceptable salt thereof, or a solvate thereof as an active ingredient.

Another aspect provides a composition for strengthening muscles or increasing exercise performance in a mammal, the composition including farnesol, a pharmaceutically acceptable salt thereof, or a solvate thereof as an active ingredient.

Still another aspect provides a composition for reducing fat, inhibiting fat accumulation, or reducing blood glucose in the body of a mammal, the composition including farnesol, a pharmaceutically acceptable salt thereof, or a solvate thereof as an active ingredient.

Still another aspect provides a composition for treating muscle fibrosis of a mammal, the composition including farnesol, a pharmaceutically acceptable salt thereof, or a solvate thereof as an active ingredient.

Farnesol is a noncyclic sesquiterpene consisting of 15 carbons, and its IUPAC name is (2E,6E)-3,7,11-trimethyl-dodeca-2,6,10-trien-1-ol. Farnesol may have a structure of the following Formula I.

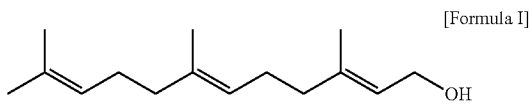 [SMILES: CC(C)=CCC/C(C)=C/CC/C(C)=C/CO]

[Formula I]

Farnesol may be purchased from a commercially available source, directly synthesized, or extracted from a natural source. The term "pharmaceutically acceptable salt" may include acid addition salts, for example, salts derived from inorganic acids such as hydrochloric acid, bromic acid, sulfuric acid, sulfamic acid, phosphoric acid, or nitric acid, and salts derived from organic salts such as acetic acid, propionic acid, succinic acid, glycolic acid, stearic acid, citric acid, maleic acid, malonic acid, methanesulfonic acid, tartaric acid, malic acid, phenyl acetic acid, glutamic acid, benzoic acid, salicylic acid, 2-acetoxybenzoic acid, fumaric acid, toluene sulfonic acid, oxalic acid, or trifluoroacetic acid, which are generally used in a pharmaceutical field, for example, in a field related to a disease caused by low expression of PGC-1α, a disease caused by overexpression of PARIS, or a disease caused by reduced farnesylation of PARIS. Further, the salt may include general metal salts, for example, salts derived from metals such as lithium, sodium, potassium, magnesium, or calcium. The acid addition salt or the metal salt may be prepared by a common method.

The term "solvate" refers to a complex or an aggregate formed by one or more solute molecules, farnesol, or pharmaceutically acceptable salts thereof and one or more solvent molecules. The solvate may be a complex or an aggregate formed with, for example, water, methanol, ethanol, isopropanol, or acetic acid.

The farnesol may be also a stereoisomer thereof. The stereoisomer may include all stereoisomers such as enantiomers and diastereomers. The farnesol may be a stereoisomerically pure form or a mixture of one or more stereoisomers, for example, a racemic mixture. Separation of a particular stereoisomer may be performed by one of the general methods known in the art.

The term "farnesylation" refers to addition of farnesyl group to cysteine residue of PARIS protein, for example, a cysteine residue of a conserved CGLS motif of PARIS protein. The CGLS motif may located near to C-terminus, for example within 100, 50, 30, or 20 amino acid residues from the C-terminus. In humans, the farnesylation may occur at C of position 631 of PARIS. The CGLS sequence (residues at positions 631-634) of an amino acid sequence of human PARIS (SEQ ID NO: 11) corresponds to the positions 638-641 of an amino acid sequence of mouse PARIS (SEQ ID NO: 10).

The term "PARIS (Parkin Interacting Substrate) may be also called ZNF746. PARIS is a kruppel associated box (KRAB) and zinc finger protein that accumulates in models of parkin inactivation and in human brain of Parkinson's disease patient.

The composition may include farnesol, a pharmaceutically acceptable salt thereof, or a solvate thereof in an effective amount. In the composition, the "effective amount" may be an amount sufficient to increase PGC-1α gene expression, to decrease PARIS gene expression, or to promote farnesylation of PARIS in a cell. The effective amount may be also an amount sufficient to convert muscle type II into muscle type I or to increase muscle type I. The effective amount may be also an amount sufficient to strengthen muscles for example, increase muscular strength or improve endurance in a mammal, or an amount sufficient to treat muscle fibrosis of a mammal. The effective amount may be also an amount sufficient to reduce fat, to inhibit fat accumulation, or to reduce blood glucose in the body of a mammal. The effective amount may be also an amount sufficient to treat sarcopenia, muscle fibrosis, muscular atrophy, obesity or diabetes. The term "treatment" means an amount sufficient to exhibit a therapeutic effect when administered to a subject in need of treatment. The term "treatment" means treatment of a disease or a medical symptom, for example, a disease caused by low expression of PGC-1α, a disease caused by overexpression of PARIS, or a disease caused by reduced farnesylation of PARIS in a subject (e.g., a mammal including a human), and it includes: (A) prevention of occurrence of a disease or a medical symptom, that is, prophylactic treatment of a patient; (b) alleviation of a disease or a medical symptom, including partial or complete treatment of the disease or medical symptom in a patient; (c) inhibition of a disease or a medical symptom, that is, delay or halt of progression of a disease or a medical symptom in a subject; or (d) relief of a disease or a medical symptom in a subject. The "effective amount" may be properly selected by those skilled in the art. The "effective amount" may be about 0.01 mg to about 10,000 mg, about 0.1 mg to about 1000 mg, about 1 mg to about 100 mg, about 0.01 mg to about 1000 mg, about 0.01 mg to about 100 mg, about 0.01 mg to about 10 mg, or about 0.01 mg to about 1 mg per kg of body weight of the subject.

The composition may be a pharmaceutical composition or a food composition. If the composition is a pharmaceutical composition, the composition may further include a pharmaceutically acceptable diluent or carrier. The carrier may be an excipient, a disintegrating agent, a binder, a lubricant, or a combination thereof. The composition may have a formulation for oral or parenteral administration. The formulation for oral administration may be a granule, a powder, a liquid, a tablet, a capsule, a dry syrup, or a combination thereof. The formulation for parenteral administration may be an injectable formulation or a formulation for skin external use. The formulation for skin external use may be a cream, a gel, an ointment, a skin emulsifier, a skin suspension, a transdermal patch, a drug-containing bandage, a lotion, or a combination thereof.

If the composition is a food composition, the composition may include one or more additives. The additive may include a concentrated fruit juice or a powder fruit juice; water-soluble or fat-soluble vitamins; a flavoring agent; amino acids, nucleic acids or salts thereof; plant fibers; or minerals. The compositions may be formulated in a variety of forms such as a powder, a granule, a tablet, a capsule, a drink, etc.

The composition may be used to treat a "muscle wasting disease". The term "muscle wasting disease" means a disease or a condition accompanied by a gradual decrease in muscle mass. The muscle may be skeletal muscle. The muscle wasting disease may be sarcopenia or muscular atrophy. Sarcopenia is the degenerative loss of skeletal muscle mass, quality, and strength associated with aging. The degenerative loss of skeletal muscle mass may be 0.5-1% loss of skeletal muscle mass per year, for example, after the age of 50. Further, sarcopenia may be defined by 1) a low muscle mass, >2 standard deviations below that mean measured in young adults (aged 18 to 39 years in the 3rd NHANES population of the same sex and ethnic background) and 2) low gait speed (e.g. a walking speed below 0.8 m/s in the 4-m walking test)). The muscle wasting disease may be caused by various factors. The muscle wasting disease may be, for example, sarcopenia caused by aging, sarcopenia caused by diabetes, sarcopenia caused by obesity, hereditary muscular atrophy, muscular atrophy caused by prolonged bed rest, muscular atrophy caused by an assistive device for therapy, or muscular atrophy caused by cachexia. The composition may be administered to a subject having the "muscle wasting disease".

The disease may be accompanied by muscle fibrosis. Muscle fibrosis is a phenomenon which frequently occurs in diseased or damaged muscle, characterized by the excessive growth of fibrous tissue and impairment of muscle function. The muscle fibrosis may be skeletal muscle fibrosis.

The composition may be used to prevent muscle loss, inhibit of muscle fibrosis, promote of muscle regeneration or differentiation, improve of exercise performance, improve a metabolic function, or a combination thereof. The composition may be used to decrease PARIS expression levels or to promote farnesylation of PARIS in a cell. The farnesylation may occur at the C position of CGLS which is a conserved C-terminal sequence of PARIS. In humans, the farnesylation may occur at C of position 631. The CGLS sequence (residues at positions 631-634) of an amino acid sequence of human PARIS (SEQ ID NO: 11) corresponds to the positions 638-641 of an amino acid sequence of mouse PARIS (SEQ ID NO: 10). This CGLS sequence is conserved in mammals as well as humans and mice, and thus C of CGLS which is located at the C-terminus of PARIS is a farnesylation site regardless of the length of the sequence.

A muscle cell or muscle fiber forming a skeletal muscle may be classified into type I muscle fiber called red muscle fiber or slow-twitch muscle fiber, and type II muscle fiber called white muscle fiber or fast-twitch muscle fiber. Type I muscle fiber appears red due to the high levels of myoglobin, and includes a large number of mitochondria and oxidase to utilize aerobic metabolism. Type I muscle fiber is characterized by slow contraction and high resistance to fatigue, and used in endurance aerobic exercise. Type II muscle fiber appears white due to the low levels of myoglobin. Type II muscle fiber is characterized by fast contraction, and is efficient for short burst of speed and strength, but has low resistance to fatigue. The composition converts type II muscle into type I among muscle fibers constituting skeletal muscles, or promotes the conversion, or increases the amount of type I muscle fiber.

The improvement of a function of metabolism may include an increase in energy expenditure, an increase in glucose tolerance, and/or a decrease in body fat content. The energy expenditure may be measured by measuring the glucose consumption amount. The glucose consumption can measured by measuring the amount of glucose at a certain interval. The glucose tolerance may measured by measuring the blood glucose level, for example, before or after the administering farnesol. The increase or decrease may be any amount, for example, an increase or decrease of about 10% or more, about 20% or more, about 30% or more, or about 40% or more than the control.

Still another aspect provides a method of increasing PGC-1α gene expression, decreasing PARIS gene expression, or promoting farnesylation of PARIS in a mammalian cell, the method including administering an effective amount of farnesol, a pharmaceutically acceptable salt thereof, or a solvate to the mammalian cell or to a subject comprising the cell. The effective amount is sufficient to increase PGC-1α gene expression, decrease PARIS gene expression, or promote farnesylation of PARIS in a mammalian cell.

The cell may be a muscle cell, such as a skeletal muscle cell. The muscle cell may be a gastrocnemius muscle (GAS) cell, a tibialis anterior muscle (TA) cell, an extensor digitorum longus muscle (EDL) cell, or a soleus muscle (SOL) cell. The cell may be in any type of mammal, particularly a human.

Farnesylation of PARIS may be increased to any degree. For example, farnesylation of PARIS may be increased by about 10% or more, about 20% or more, about 30% or more, or about 40% or more than a control. Farnesylation may occur at a cysteine residue at position 631 of PARIS, as described above with respect to the compositions described herein.

The method may be used to treat a disease caused by low expression of PGC-1α, a disease caused by overexpression of PARIS, or a disease caused by reduced farnesylation of PARIS.

The low expression of PGC-1α may be a low expression level of PGC-1α gene in a muscle cell compared to that of a muscle cell of the same type derived from a control subject, for example, a healthy person; or a low expression level of PGC-1α gene in a subject compared to the previous expression level of PGC-1α gene in the same subject within a predetermined previous period, for example, before about 1 year, about 300 days, about 200 days, about 100 days, about 50 days, about 30 days, or about 10 days (e.g., a patient with decreasing PGC-1α expression levels over time); or a low expression level of PGC-1α gene compared to a predetermined level. The predetermined level refers to a level of a control. The control may be a normal healthy person or a population of normal healthy people. Thus, the predetermined value may an average expression level of a population of normal healthy people. The low expression of PGC-1α may include no expression of PGC-1α gene. Low expression of PGC-1α may be, for instance, a PGC-1α expression level that is reduced by about 10% or more, about 20% or more, about 30% or more, or about 40% or more compared to the control.

Overexpression of PARIS gene may be an expression level of PARIS gene in a muscle cell that is higher than that of a muscle cell of the same type derived from a control subject, for example, a healthy person, a high expression level of PARIS gene; or an expression level of PARIS in a subject that is higher than that of the same patient in a predetermined previous period, for example, before about 1 year, about 300 days, about 200 days, about 100 days, about 50 days, about 30 days, or about 10 days (e.g., a subject with PARIS expression levels that are increasing over time); or a high expression level of PARIS gene compared to a predetermined level. The predetermined level refers to a level of a control. The control may be a normal healthy person or a population of normal healthy people. Thus, the predetermined value may an average expression level of a population of normal healthy people. The overexpression may be an expression level increased by any amount, such as about 10% or more, about 20% or more, about 30% or more, or about 40% or more compared to the control.

Reduced farnesylation of PARIS includes a low farnesylation level of PARIS in a muscle cell of a subject compared to that of a muscle cell derived from a control subject, for example, a healthy person; a low farnesylation level of PARIS in a subject compared to that of the same subject before a predetermined period, for example, before about 1 year, about 300 days, about 200 days, about 100 days, about 50 days, about 30 days, or about 10 days (e.g., a subject with farnesylation levels of PARIS that is decreasing over time); or a low farnesylation level of PARIS, compared to a predetermined level. The predetermined level refers to a level of a control. The control may be a normal healthy person or a population of normal healthy people. Thus, the predetermined value may an average expression level of a population of normal healthy people. Reduced farnesylation may be, for example, a farnesylation level that is about 10% or less, about 20% or less, about 30% or less, or about 40% or less than that of the control.

In the forgoing methods, the farnesol (or salt or solvate thereof) may be administered to a subject who exhibits low expression of PGC-1α gene, overexpression of PARIS gene, or reduced farnesylation of PARIS in a cell. Also, farnesol (or salt or solvate thereof) may be administered to a subject having a disease caused by the low expression of PGC-1α gene, a disease caused by the overexpression of PARIS gene, or a disease caused by the reduced farnesylation of PARIS. The subject may be a subject having a muscle wasting disease.

Administration of farnesol to a subject in accordance with the foregoing methods is believed to have the effect of increasing PGC-1α gene expression, decreasing PARIS gene expression, or promoting farnesylation of PARIS in a mammalian cell or subject, thereby alleviating a symptom or treating a disease associated with low levels of PGC-1α gene expression, increased PARIS gene expression, or low levels of farnesylation of PARIS.

Still another aspect provides a method of converting muscle type II into muscle type I in a subject, or increasing muscle type I in a subject, the method including administering an effective amount of farnesol, a pharmaceutically acceptable salt thereof, or a solvate to a subject. The effective amount may be an amount sufficient to convert muscle type II into muscle type I, to promote the conversion, or to increase muscle type I. The administration may be administration to a subject in which the amount of muscle type I is reduced (e.g., having a low level of type I) compared to that of a control subject, for example, a normal healthy subject; or a low level of type I muscle in a subject compared to the level of type I muscle in the same subject before a predetermined period, for example, before about 1 year, about 300 days, about 200 days, about 100 days, about 50 days, about 30 days, or about 10 days (e.g., a subject with decreasing amounts of type I muscle over time); or a low level of type I, compared to a predetermined level. The predetermined level refers to a level of a control. The control may be a normal healthy person or a population of normal healthy people. Thus, the predetermined value may an average expression level of a population of normal healthy people.

Still another aspect provides a method of strengthening muscles in a mammal, the method including administering an effective amount of farnesol, a pharmaceutically acceptable salt thereof, or a solvate to a subject. The effective amount may be an amount sufficient to strengthen muscles or to increase exercise performance.

Strengthening muscles includes a relative increase in an amount of type I muscle, compared to that of type II muscle, in a subject; an increase in oxidative metabolism; an increase in grip strength; or a combination thereof. The subject may be a subject in which muscles are weakened or exercise performance is weakened as compared to a normal healthy subject of the same type. The weakening may be a relatively low level of type I muscle, a low oxidative metabolism, a low grip strength, or a combination thereof, compared to that of a muscle cell derived from a control subject, for example, a healthy subject; or a relatively low level of type I muscle, a low oxidative metabolism, a low grip strength, or a combination thereof, compared to that of the same subject before a predetermined period, for example, before about 1 year, about 300 days, about 200 days, about 100 days, about 50 days, about 30 days, or about 10 days (a subject with decreasing type I muscle, oxidative metabolism, grip strength, or combination thereof, over time); or a low level of type I muscle, a low oxidative metabolism, a low grip strength, or a combination thereof, compared to a predetermined level. The predetermined level refers to a level of a control. The control may be a normal healthy person or a population of normal healthy people. Thus, the predetermined level may an average expression level of a population of normal healthy people. The subject may be a subject suffering from hypokinesia due to muscle injury. Strengthening muscles also include strengthen muscular strength and/or improve endurance.

Still another aspect provides a method of reducing fat (e.g., body fat), inhibiting fat accumulation, or reducing blood glucose in the body of a mammal, the method including administering an effective amount of farnesol, a pharmaceutically acceptable salt thereof, or a solvate to a subject. The fat may be brown fat, white fat, and/or visceral fat. The fat may be fat in the muscle tissue. The farnesol or salt or solvate thereof may be administered to a subject showing increased fat or blood glucose level, or otherwise in need of a reduction in fat or blood glucose level. The increase may be a high level of fat or blood glucose, compared to a control subject, for example, a healthy person; or a high level of fat or blood glucose in a subject compared to that of the same subject before a predetermined period, for example, before about 1 year, about 300 days, about 200 days, about 100 days, about 50 days, about 30 days, or about 10 days (e.g., a subject with increasing amounts of fat or blood glucose); or a high level of fat or blood glucose, compared to a predetermined level. The predetermined level refers to a level of a control. The control may be a normal healthy person or a population of normal healthy people. Thus, the predetermined level may an average expression level of a population of normal healthy people. The amount of fat or blood glucose may be reduced by any amount, such as by about 10% or more, about 20% or more, about 30% or more, or about 40% or more compared to the control, or such that the method provides a fat or blood glucose level that is about 10% or less, about 20% or less, about 30% or less, or about 40% or less than that of the control.

Still another aspect provides a method of treating muscle fibrosis of a subject, the method including administering an effective amount of farnesol, a pharmaceutically acceptable salt thereof, or a solvate thereof to the subject.

In any of the foregoing methods, the administration may be performed by a method known in the art. The administration may be, for example, intravenous, intramuscular, oral, transdermal, mucosal, intranasal, intratracheal, or subcutaneous administration. The administration may be systemic or topical administration. The administration may be topical administration to a site in which exercise performance is reduced. The administration may be administration to muscle tissues. The administration may be administration to skeletal muscles. The muscles may be skeletal muscles. The skeletal muscles may be facial muscles, neck muscles, abdominal muscles, back muscles, pectoral muscles, upper limb muscles, or lower limb muscles. The lower limb muscles may be gastrocnemius muscles (GAS), tibialis anterior muscles (TA), extensor digitorum longus muscles (EDL), or soleus muscles (SOL).

In any of the foregoing methods, the subject may be any subject in need of treatment, particularly a mammal such as a human. In one embodiment, the subject may be a person aged 50 years or over, or a person aged 60 years or over, for example, a person aged about 50 years to about 100 years, about 60 years to about 100 years, about 70 years to about 100 years, about 80 years to about 100 years, about 90 years to about 100 years, about 60 years to about 90 years, about 60 years to about 80 years, or about 60 years to about 70 years. Age, as referred to herein, means the chronological age calculated from birth.

In any of the foregoing methods, the administration may be performed by administration in any suitable amount, such as an amount of about 0.1 mg to about 1,000 mg, about 0.1 mg to about 500 mg, about 0.1 mg to about 100 mg, about 0.1 mg to about 50 mg, about 0.1 mg to about 25 mg, about 1 mg to about 1,000 mg, about 1 mg to about 500 mg, about 1 mg to about 100 mg, about 1 mg to about 50 mg, about 1 mg to about 25 mg, about 5 mg to about 1,000 mg, about 5 mg to about 500 mg, about 5 mg to about 100 mg, about 5 mg to about 50 mg, about 5 mg to about 25 mg, about 10 mg to about 1,000 mg, about 10 mg to about 500 mg, about 10 mg to about 100 mg, about 10 mg to about 50 mg, or about 10 mg to about 25 mg per kg of body weight per day.

In any of the foregoing methods, the subject may be a mammal, for example, a human, a cow, a horse, a pig, a dog, a sheep, a goat, or a cat. In some embodiments, the subject may be a mammal excluding a human. The subject may be a subject in need of increasing red muscle fiber, slow-twitch muscle fiber, or type I muscle fiber. The subject may be a mammal having a disease caused by low expression of PGC-1α, a disease caused by overexpression of PARIS, or a disease caused by reduced farnesylation of PARIS, or a mammal in need of prevention of muscle loss, inhibition of muscle fibrosis, promotion of muscle regeneration or differentiation, improvement of exercise performance, improvement of a function of metabolism, or a combination thereof.

In the above aspects, the method may further include measuring an expression level of PGC-1α gene, an expression level of PARIS gene, or a farnesylation level of PARIS in a mammalian cell. The expression level may be a level of mRNA or protein expressed from the gene. The measuring may be performed by a known method of measuring a protein or mRNA. The measuring may be performed by one or more selected from the group consisting of RT-PCR, Northern blotting, microarray, Western blotting, enzyme-linked immunosorbent assay, immunohistochemistry, immunoprecipitation, complement fixation assay, flow cytometry, protein chip assay, chromatography, precipitation, salting out, mRNA separation and protein separation.

The administration may be administration to a subject showing a low expression level of PGC-1α gene, an overexpression level of PARIS gene, or a reduced farnesylation level of PARIS, when measured. The "low expression", "overexpression", or "reduced farnesylation" is the same as described above.

Still another aspect provides a method of exploring (screening for) a material or composition capable of reducing PGC-1α expression in a mammalian cell, the method including contacting a candidate material with the mammalian cell; and measuring an expression level of PARIS gene or a farnesylation level of PARIS protein in the cell.

The method includes contacting a candidate material with a mammalian cell. The contacting may be performed in a liquid or solid. The liquid may be, for example, water, a proper buffer (e.g., PBS), or physiological saline. The candidate material may be any molecule or material. The candidate material may be a low molecular weight compound, a protein, a nucleic acid, or a sugar. The mammalian cell may be a muscle cell. The muscle may be a skeletal muscle. The skeletal muscle may be a facial muscle, a neck muscle, an abdominal muscle, a back muscle, a pectoral muscle, an upper limb muscle, or a lower limb muscle. The lower limb muscle may be a gastrocnemius muscle (GAS), a tibialis anterior muscle (TA), an extensor digitorum longus muscle (EDL), or a soleus muscle (SOL). The cell may be a cell separated or a cell in a tissue, for example, a muscle tissue. The candidate material or cell may be immobilized on a substrate to form an array. The array may be a microarray, for example, a cell-immobilized microarray.

The method includes measuring the expression level of PARIS gene or the farnesylation level of PARIS protein in the cell. The measuring may be performed by nucleic acid amplification, for example, one or more selected from the group consisting of PCR, RT-PCR, Northern blotting, microarray, Western blotting, enzyme-linked immunosorbent assay, immunohistochemistry, immunoprecipitation, complement fixation assay, flow cytometry, protein chip assay, chromatography, precipitation, salting out, and protein separation. The expression level of PARIS gene may be a level of mRNA or PARIS protein expressed.

The method may further include determining the candidate material as a material capable of reducing PGC-1α expression in the mammalian cell when the expression level of PARIS gene is reduced or the farnesylation level of PARIS protein is increased, compared to a mammalian cell of the same type which is not contacted with the candidate material. The farnesylation may occur at the cysteine residue at position 631 of PARIS. The candidate material which is determined as a material capable of reducing PGC-1α expression in the mammalian cell may be a candidate material capable of treating a muscle wasting disease, for example, sarcopenia, muscle fibrosis, muscular atrophy, obesity or diabetes.

Still another aspect provides a method of determining exercise performance in a mammalian subject, the method including measuring the expression level of PARIS gene or the farnesylation level of PARIS protein in a cell of the mammalian subject; and comparing the obtained expression level of PARIS gene or the obtained farnesylation level of PARIS protein with a predetermined value.

The method includes measuring the expression level of PARIS gene or the farnesylation level of PARIS protein in a cell of the mammalian subject. The expression level of PARIS gene may be a level of mRNA or PARIS protein expressed. The measuring may be performed by nucleic acid amplification, for example, one or more selected from the group consisting of PCR, RT-PCR, Northern blotting, microarray, Western blotting, enzyme-linked immunosorbent assay, immunohistochemistry, immunoprecipitation, complement fixation assay, flow cytometry, protein chip assay, chromatography, precipitation, salting out, and protein separation.

The cell may be a muscle cell. The muscle may be a skeletal muscle. The skeletal muscle may be a facial muscle, a neck muscle, an abdominal muscle, a back muscle, a pectoral muscle, an upper limb muscle, or a lower limb muscle. The lower limb muscle may be a gastrocnemius muscle (GAS), a tibialis anterior muscle (TA), an extensor digitorum longus muscle (EDL), or a soleus muscle (SOL). The cell may be a cell separated or a cell in a tissue, for example, a muscle tissue.

The method includes comparing the obtained expression level of PARIS gene or the obtained farnesylation level of PARIS protein with a predetermined value. The predetermined value may be an expression level of PARIS gene or a farnesylation level of PARIS protein in a control group, for example, the level of a normal healthy person, or a level in the same person before a predetermined period, for example, before about 1 year, about 300 days, about 200 days, about 100 days, about 50 days, about 30 days, or about 10 days. The control group may be the level of a healthy person aged 20 to 60 years, for example, about 20 to 50 years, 20 to 40 years, 20 to 30 years, 30 to 60 years, 40 to 60 years, or 50 to 60 years.

The method may further include determining that the subject sufficiently exercises (e.g., has sufficient or high muscle strength) when the expression level of PARIS gene thus obtained is equal to or lower than a predetermined value; or determining that the subject does not sufficiently exercise (e.g., has low or insufficient muscle strength) when the expression level of PARIS gene thus obtained is higher than the predetermined value; or determining that the subject sufficiently exercises (e.g., has sufficient or high muscle strength) when the farnesylation level of PARIS protein thus obtained is equal to or higher than the predetermined value; or determining that the subject does not sufficiently exercise (has low or insufficient muscle strength) when the farnesylation level of PARIS protein thus obtained is lower than the predetermined value. The predetermined value may the level of a normal healthy person or the level of the same subject before performing the exercise. The predetermined value may be the expression level of PARIS gene that is about 1% or lower, about 3% or lower, about 5% or lower, about 10% or lower, about 20% or lower, about 30% or lower, about 40% or lower, or about 50% or lower than the expression level of PARIS gene of the same subject before performing the exercise. The predetermined value is the farnesylation level of PARIS protein that is about 1% or lower, about 3% or lower, about 5% or lower, about 10% or higher, about 20% or higher, about 30% or higher, about 40% or higher, or about 50% or higher than the farnesylation level of PARIS protein of the same subject before performing exercise. The exercise may be an aerobic exercise such running, walking, swimming etc. The exercise may be a running or walking on a treadmill.

In another embodiment, the method comprises measuring the expression level of PARIS gene or the farnesylation level of PARIS protein a subject within particular time, for example, 1 hour or other suitable time frame after performing an exercise of a specific intensity and duration, and comparing the measured expression level of PARIS gene or the farnesylation level of PARIS protein to a control, which may be the predetermined level of a normal healthy person after performing the same exercise or at rest (not having performed exercise of any substantial intensity within 1 hour of testing), or to the level of the same subject before performing the exercise. The method may further include determining that the subject sufficiently exercises (e.g., has sufficient or high muscle strength) when the expression level of PARIS gene thus obtained is equal to, or lower than, the control; or determining that the subject does not sufficiently exercise (e.g., has low or insufficient muscle strength) when the expression level of PARIS gene thus obtained is higher than the control; or determining that the subject sufficiently exercises (e.g., has sufficient or high muscle strength) when the farnesylation level of PARIS protein thus obtained is equal to or higher than the control; or determining that the subject does not sufficiently exercise (has low or insufficient muscle strength) when the farnesylation level of PARIS protein thus obtained is higher than the control.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in further detail with reference to Examples. However, these Examples are for illustrative purposes only and are not intended to limit the scope of the present invention.

Example 1: Screening of PGC1-α Activator

1. Establishment of PGC-1α Reporter-Expressing C2C12 Myoblast

C2C12 myoblast is purchased from ATCC (Cat no. CRL-1722, American Type Culture Collection, USA). To screen for a compound activating PGC-1α gene expression in C2C12 myoblast, a PGC-1α reporter-expressing C2C12 cell line (hereinafter, referred to as 'PGC-1α reporter cell line' or 'C2C12-PGC-1α cell line) is established. A vector expressing luciferase and dscGFP (destabilized Green Fluorescent Protein) under human PGC-1α promoter having a length of 1 kb is prepared, and this vector is inserted into lentivirus to transfect C2C12 cells. To select a cell line that genetically and stably expresses this vector, fluorescence emitted from green fluorescent protein (GFP) included in the vector is monitored. 5 µg/ml of puromycin, a selection marker for this vector, is added to a cell culture medium, and a cell line expressing PGC-1α reporter is selected. A luciferase expression level in the PGC-1α reporter cell depends on a stimulation applied to the PGC-1α promoter. That is, if a compound is a PGC-1α expression inducer, it stimulates the PGC-1α promoter to increase the luciferase expression, and if a compound is a PGC-1α expression inhibitor, the luciferase expression is decreased. The expression level is measured by luminescence after addition of a luciferase substrate, thereby determining activation or inhibition of PGC-1α transcription by the compound.

2. Screening of Compound Using PGC-1α Reporter Cell Line

The C2C12-PGC-1α reporter cell line prepared in Section 1 is used to screen a PGC-1α expression regulator from 2320 compounds provided by Korea chemical bank. In detail, C2C12-PGC-1α reporter cells are cultured in each well of 96-well plate containing DMEM (Dulbecco's modified Eagle's medium, Gibco) supplemented with 10% fetal bovine serum (FBS) in a 5% $CO_2$ incubator until they reach 70% confluence by changing the medium every 2 days. Thereafter, 2320 compounds are dissolved in DMSO at a final concentration of 10 µM, and then added to each well. 48 hours later, luminescence by luciferase is measured. in detail, cells are lysed in 10 µl of passive lysis buffer (50 mM Tris-HCl, 7.5 mM $MgCl_2$, 750 mM NaCl, 5 mM EGTA, 1% Triton-x 100, 1 mM $Na_3VO_4$, 10 mM NaF, 0.1 mM PMSF (phenylmethanesulfonylfluoride), PI (protease inhibitor)) as a cell lysis buffer, and 50 µl of a luciferase substrate, luciferin was added thereto to allow enzymatic reaction. Then, luminescence is measured. The measured values are normalized to each well and plate, and a value measured in a well treated with a solvent of the compound, DMSO is used as a control group to express the value as a relative ratio. PGC-1α promoter activities of 2320 compounds are measured, and as a result, 8 compounds ranked in the top 1.5%, which show promoter activity twice or higher than that of a control group DMSO, are selected. Among 8 compounds, farnesol greatly increasing the PGC-1α promoter activity and having high safety is selected as a candidate material. Farnesol is used as a food additive, and its lethal dose (LD) for 50% mouse mortality is 8,765 mg per mouse body weight (kg). Farnesol is found in the body, and also in various plants and fruits. It is extracted therefrom and used as a natural compound. For reference, ID50 of aspirin is 250 mg/kg.

Example 2: Effect of Farnesol on Myoblast and Skeletal Muscle

1. Analysis of Differentiation Markers in Farnesol-Treated Myoblasts

DMEM (Dulbecco's Modified Eagle Medium) supplemented with 10% fetal bovine serum is used as a growth medium for culture of C2C12 myoblasts, and DMEM supplemented with 2% horse serum is used as a differentiation medium for differentiation of muscle cells. To induce differentiation of C2C12 myoblasts into muscle cells, 0.1 µM farnesol dissolved in DMSO or various concentrations of farnesol (0.1, 1, 10, 100 uM) are added, and DMSO is only added to a control group. The cells are cultured for 48 hours to induce differentiation, and then a lysis buffer (20 mM Tris-HCl, pH 8, 150 mM NaCl, 1% Triton X, Proteinase Inhibitor) is added to the harvested cells to allow lysis for 30 minutes, followed by centrifugation at 13,000 rpm for 30 minutes. The amount of protein in the cell lysis sample is quantified and an equal amount of protein is subjected to 8%

SDS-PAGE. The protein is transferred onto a PVDF membrane, and then incubated in a blocking buffer containing 5% skim milk for 1 hour. HRP (horseradish peroxidase)-conjugated rabbit antibodies specific to individual proteins, diluted in 5% BSA, are reacted with the membrane at 4° C. for 12 hours, and then the membrane is washed with a wash buffer for 5 minutes three times. Thereafter, the membrane is exposed to X-ray film using an ECL reagent (Roche) to confirm protein expression levels.

FIG. 1A shows expression changes of PGC-1α and muscle differentiation markers by treatment of myoblast with farnesol. As shown in FIG. 1A, farnesol-treated myoblasts show about 2.8 times increase in PGC-1α gene expression, compared to a control group. Further, expressions of myogenic markers, myoblast determination protein (MyoD) and myosin heavy chain (MHC), and troponin T gene are increased by treatment of farnesol.

Figure 1B:
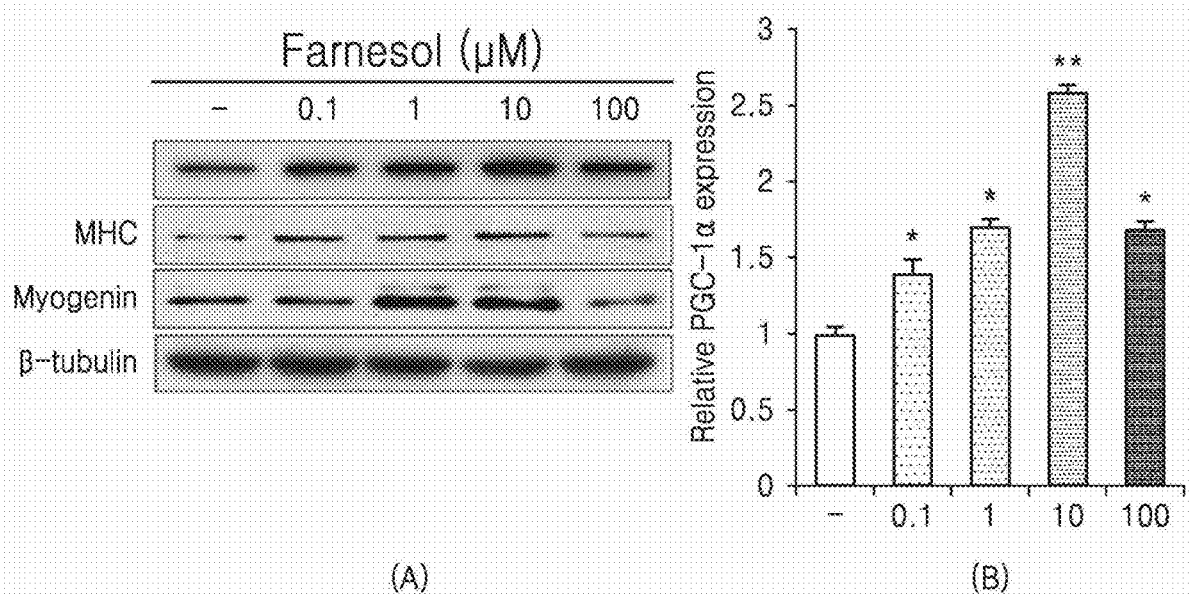
FIG. 1B shows expression changes of PGC-1α and muscle differentiation markers in myoblasts according to farnesol concentration (0.1-100 uM)

FIG. 1B shows expression changes of PGC-1α and muscle differentiation markers in myoblasts according to farnesol concentration (0.1-100 uM). In FIG. 1b, A shows an image of a membrane obtained by Western blotting, B shows a relative expression obtained by quantifying a PGC-1α band in the Western blotting image of A and comparing it with that of a non-farnesol treated control group. As shown in FIG. 1B, expressions of PGC-1α and muscle differentiation markers, MHC and myogenin are increased in myoblasts in a farnesol concentration-dependent manner within a predetermined concentration range, for example, from 0.1 to 10 uM. The results of FIGS. 1A and 1B indicate that farnesol promotes differentiation of myoblast into muscle.

2. Analysis of PGC-1α Expression and Muscle Change in Farnesol-Treated Mouse 5 month-old C57BL/6 male mice (weighing 22 g) are maintained at a temperature of 22±2° C., humidity of 55±5%, and a light-dark cycle of 12:12 hours. An animal feed containing 0.5% w/w farnesol was supplied by Jung-Ang Lab Animal Inc. A control group is fed with a feed equivalent to a general feed for experimental animals, excluding that no 0.5% w/w farnesol is contained. They are allowed free access to drinking water. Skeletal muscles were separated from the mice and control mouse fed with farnesol for 5 weeks, and subjected to immunoblot analysis. In all the following Examples, administration or feeding of mouse is performed as above, unless otherwise mentioned. A 5-month-old mouse is comparable to a 30-old human, based on a ratio of mouse life expectancy to human life expectancy. In this specification, assuming that human life expectancy of 100 years corresponds to mouse life expectancy of 3 years, human life expectancy is estimated from the relationship.

Figure 1C:
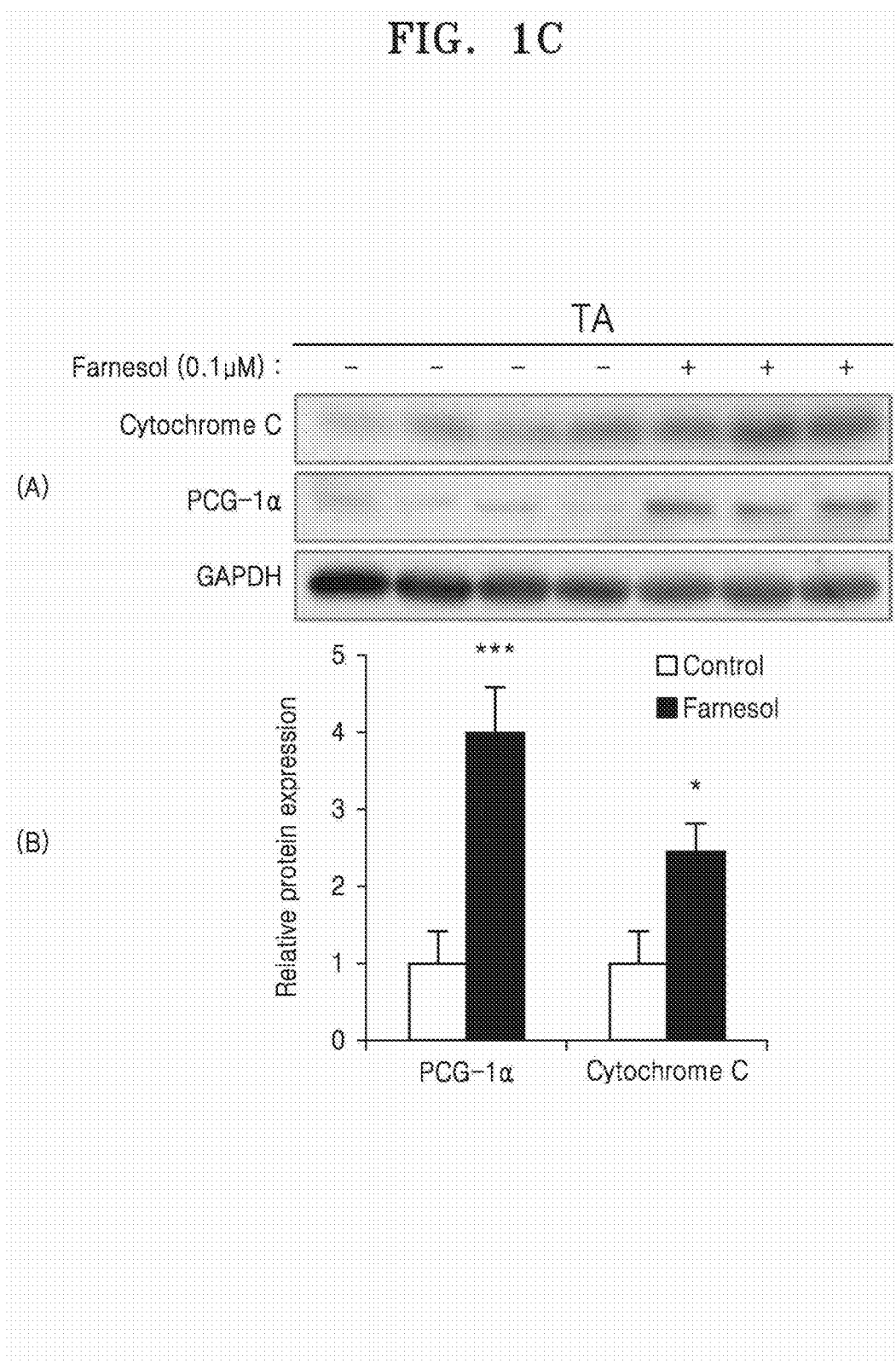
FIG. 1C shows results of immunoblotting of tibialis anterior muscles of mice administered with farnesol.

FIG. 1C shows results of immunoblotting of tibialis anterior muscles of mice administered with farnesol. *Standard error of measurement indicates P<0.05. In FIG. 1c, A shows an image of a membrane obtained by Western blotting, B shows a relative protein expression obtained by quantifying a PGC-1α band and a cytochrome C band in the Western blotting image of A and comparing them to the value of a non-farnesol treated mouse. As shown in FIG. 1c, expressions of PGC-1α and a mitochondrial protein, cytochrome C are increased, compared to the control group ('-' in A of FIG. 1C represents a non-farnesol treated control group, indicating that increased expression of PGC-1α by administration of farnesol increases expression of cytochrome C in skeletal muscles.

Figure 1D:
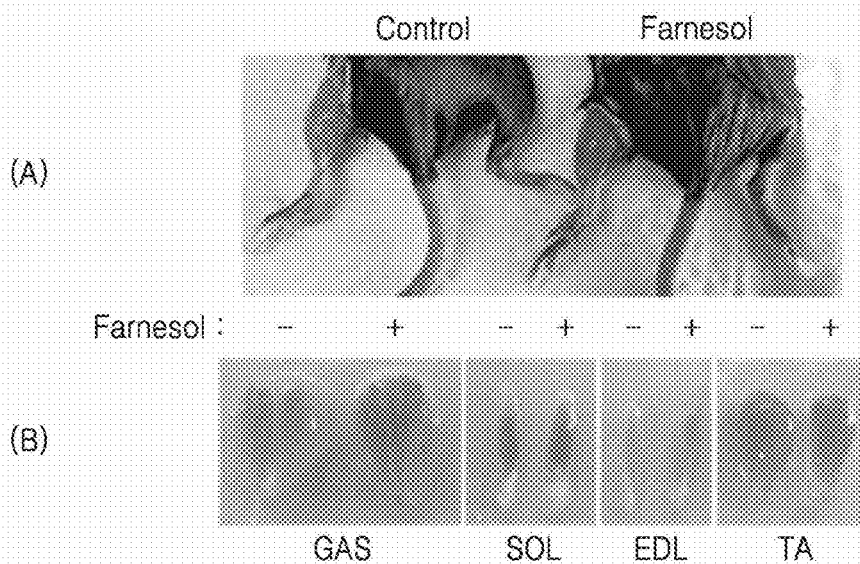
FIG. 1D shows results of observing lower limb muscles of mice administered with farnesol.

To evaluate functional consequence of PGC-1α increased by farnesol treatment of skeletal muscle, lower limb muscles of mice fed with farnesol for 5 weeks are analyzed. FIG. 1D shows results of observing lower limb muscles of mice administered with farnesol. In FIG. 1D, panel A is an image showing lower limb muscles of a control group and an experimental mouse, panel B shows 4 different muscles separated from mice, that is, GAS, SOL, EDL, and TA. Herein, GAS indicates gastrocnemius muscle, SOL indicates soleus muscle, EDL indicates extensor digitorum longus muscle, and TA indicates tibialis anterior muscle. Gastrocnemius muscle exists as a white muscle because glycolytic muscle fibers are mainly distributed therein. As shown in FIG. 1D, muscle fibers of gastrocnemius muscle, soleus muscle, extensor digitorum longus muscle, and tibialis anterior muscle are converted to red muscles having a high percentage of oxidative muscle fibers in the farnesol-treated mouse, compared to the control group, indicating that increased expression of PGC-1α by farnesol treatment increases oxidative muscle fibers in gastrocnemius muscle, soleus muscle, extensor digitorum longus muscle, and tibialis anterior muscle.

3. Observation of Muscle Fiber in Farnesol-Treated Mouse

To examine distribution of 2a type muscle fiber and 2b type muscle fiber, extensor digitorum longus muscles of mice administered with farnesol for 5 weeks are subjected to immunohistochemistry. 2a type muscle fiber is an oxidative muscle fiber type, and there are two types: aerobic, that is, oxygen-dependent energy source and anaerobic, that is, oxygen-independent energy source. 2b type muscle fiber is a glycolytic muscle fiber type, and includes only anaerobic energy source. Frozen sections stored in a deep freezer of −80° C. are washed with 1×PBS twice, and fixed with 4% paraformaldehyde at room temperature for 15 minutes, and then washed with 1×PBS twice. The tissue and a permeabilization buffer (0.2% Triton-X/PBS) are reacted at room temperature for 30 minutes, and washed with 1×PBS twice. The tissue and Proteinase K are reacted at 37° C. for 10 minutes for antigen retrieval, and washed with 1×PBS twice, and blocked in a blocking buffer (0.1% gelatin, 5% goat serum, 0.5% BSA, and 0.1% Triton-X) for 1 hr. As a primary antibody, a rabbit antibody specifically binding to MHC2a or MHC2b is diluted with the blocking buffer at a ratio of 1:500 and reacted at 4° C. for 12 hrs, followed by washing with 1×PBS twice. A secondary antibody, anti-rabbit antibody is reacted, followed by washing 1×PBS twice. After sealing, a fluorescence microscope (Nikon, body: Ti-u, camera: DS-RI1, program: NIS-elements BR 3.1) was used for analysis.

Figure 1E:
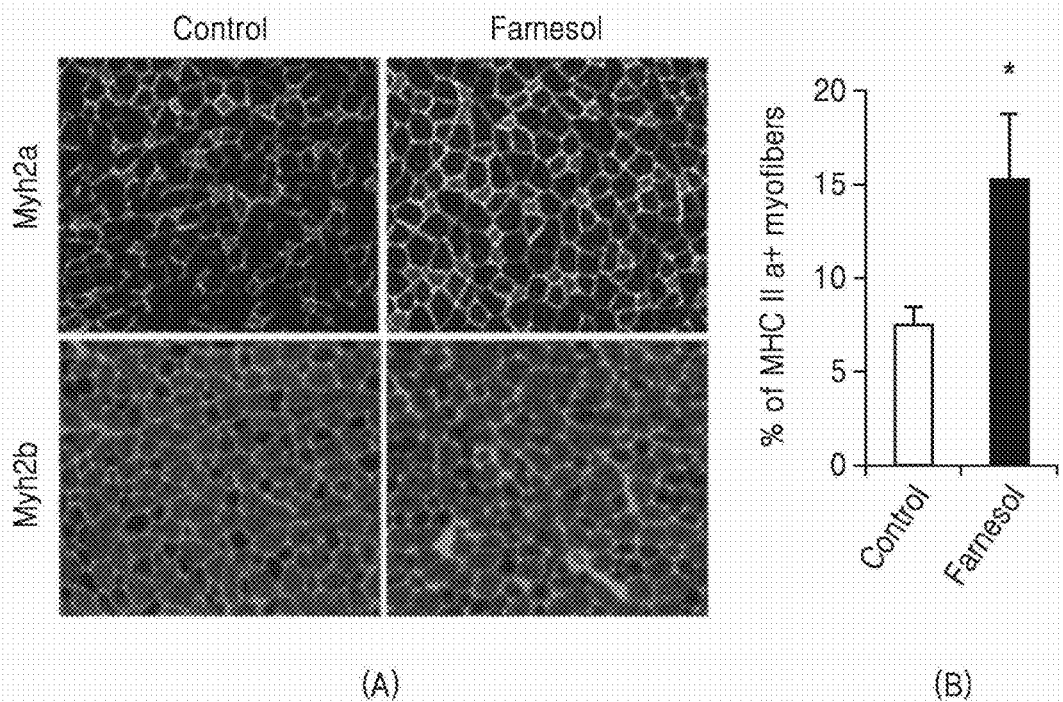
FIG. 1E shows changes of the muscle fiber type in the extensor digitorum longus muscles of farnesol-treated mouse.

FIG. 1E shows changes of the muscle fiber type in the extensor digitorum longus muscles of farnesol-treated mouse. In FIG. 1E, A shows results of performing immunohistochemistry of the frozen sections of extensor digitorum longus muscles using rabbit anti-myh2a antibody and anti-myh2b antibody, and B shows the number of muscle fibers in which Myh2a is stained and colored green. In A, the green color represents muscle fibers stained with anti-Myh2a antibody. As shown in FIG. 1E, the number and diameter of oxidative 2a type muscle fiber are increased in the extensor digitorum longus muscle of mouse orally administered with farnesol, compared to those of the muscle of a non-farnesol treated control mouse. In contrast, the number of glycolytic 2b type muscle fiber is decreased, indicating that farnesol treatment increases oxidative muscle fibers having high mitochondrial activity and decreases glycolytic muscle fibers.

4. Analysis of Mitochondrial Enzyme Activity in Farnesol-Administered Mouse

Staining of succinic dehydrogenase (SDH) in the extensor digitorum longus muscle of a mouse administered with farnesol for 5 weeks is performed. This staining method is a method of analyzing mitochondrial activity by measuring activity of SDH which is an enzyme involved in the electron transport chain of mitochondria. Staining degree represents a content of oxidative muscle fiber. Frozen tissue sections are reacted in 0.2 M phosphate buffer (pH 7.4) containing 50 uM sodium succinate and nitro blue tetrazolium (NBT) at 37° C. for 60 minutes, washed with distilled water, and then sealed, followed by observation.

Figure 1F:
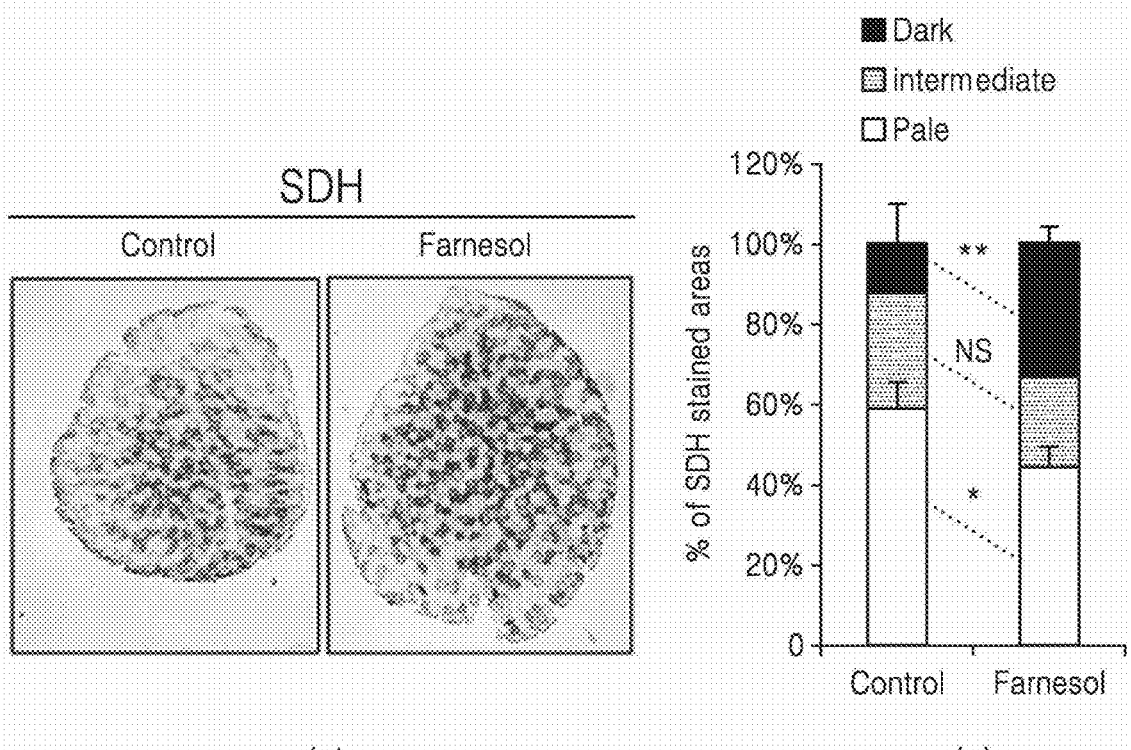
FIG. 1F shows changes in activity of a mitochondrial enzyme SDH in the extensor digitorum longus muscle of farnesol-administered mouse.

FIG. 1F shows changes in activity of a mitochondrial enzyme SDH in the extensor digitorum longus muscle of farnesol-administered mouse. In FIG. 1F, A is an image showing result of staining the frozen tissue sections, and B shows a percentage of stained areas of A, which are classified into three intensities of dark, intermediate, and pale. As shown in FIG. 1F, a percentage of the area stained dark is remarkably increased, that is, a percentage of muscle fiber having an increased SDH activity is increased in the extensor digitorum longus muscle of farnesol-administered mouse, compared to a control group, indicating that farnesol treatment activates mitochondrial energy metabolism in muscle fibers.

Such results of Example 2 suggest that farnesol increases oxidative metabolism in myoblasts and skeletal muscles. The increase of oxidative metabolism is attributed to induction of PGC-1α expression by farnesol.

5. Analysis of Amount of Intracellular Farnesol or Metabolite Thereof in Farnesol-Administered Mouse The amount of intracellular farnesol or metabolite thereof is measured in the extensor digitorum longus muscle of a mouse administered with farnesol for 5 weeks.

Sample pretreatment for quantitative analysis of farnesol in the mouse extensor digitorum longus muscle is performed by extraction using saturated KOH/ethanol and fractionation using Tris-HCl buffer and n-hexane: ethanol (Journal of Pharmaceutical and Biomedical Analysis 47(2008) 560-566) and an n-hexane layer is obtained and dried, followed by LC-MS/MS (ACQUITY UPLC System and ACQUITY TQD mass spectrometry, Waters). As a column, Hypersil Aq Gold C18 (100×2.1 mm, 1.9 um, thermo scientific) is used, and as a mobile phase, A (0.1% formic acid in water) and B (0.1% formic acid in acetonitrile) are used with the following gradient conditions: 0-3 min (40% B), 3-10 min (40-85% B), 10-15 min (85% B), 15-16 min (85-40% B), and 16-21 min (40% B). A column temperature is 40° C., and a flow rate is 200 um/min. Detection of farnesol and 1-tetradecanol used as an internal standard is performed using the following mass parameter: positive ion mode, cone voltage (27 V), capillary (3 kV), source temperature (140° C.), desolvation temperature (350° C.), cone gas (70 L/h), desolvation gas (900 L/h). MS/MS transition conditions are 205.2→121.1 and collision energy of 17 eV for farnesol and 197.3→71.0 and collision energy of 7 eV for 1-tetradecanol. The concentration of farnesol is determined by a ratio of a peak area of farnesol to a peak area of 1-tetradecanol used as an internal standard, they are added to the sample in an equal amount.

Sample pretreatment for quantitative analysis of a farnesol metabolite, farnesylpyrophosphate (FPP) in the mouse extensor digitorum longus muscle is performed by extraction using 2-propanol: 100 mM $NH_4HCO_3$, pH 7.8 (1:1 v/v) and protein precipitation using acetonitrile (Anal. Biochem. 383 (2008) 18-24), and a supernatant is obtained and dried, followed by LC-MS/MS (ACQUITY UPLC System and ACQUITY TQD mass spectrometry, Waters). As a column, Hypersil Aq Gold C18 (100×2.1 mm, 1.9 um, thermo scientific) is used, and as a mobile phase, A (20 mM ammonium bicarbonate and 0.1% triethylamine in water) and B (0.1% triethylamine in acetonitrile) are used with the following gradient conditions: 0-2 min (2% B), 2-12 min (2-95% B), 12-14 min (95% B), 14-14.5 min (95-2% B), and 14.5-20 min (2% B). A column temperature is 40° C., and a flow rate is 300 um/min. Detection of farnesylpyrophosphate (FPP) is performed using the following mass parameter: negative ion mode, cone voltage (40 V), capillary (2.5 kV), source temperature (130° C.), desolvation temperature (450° C.), cone gas (50 L/h), desolvation gas (900 L/h). MS/MS transition conditions are 381.2→78.9 and collision energy of 22 eV for the farnesol metabolite (farnesylpyrophosphate, FPP). The concentration of FPP is determined by a peak area.

Figure 1G:
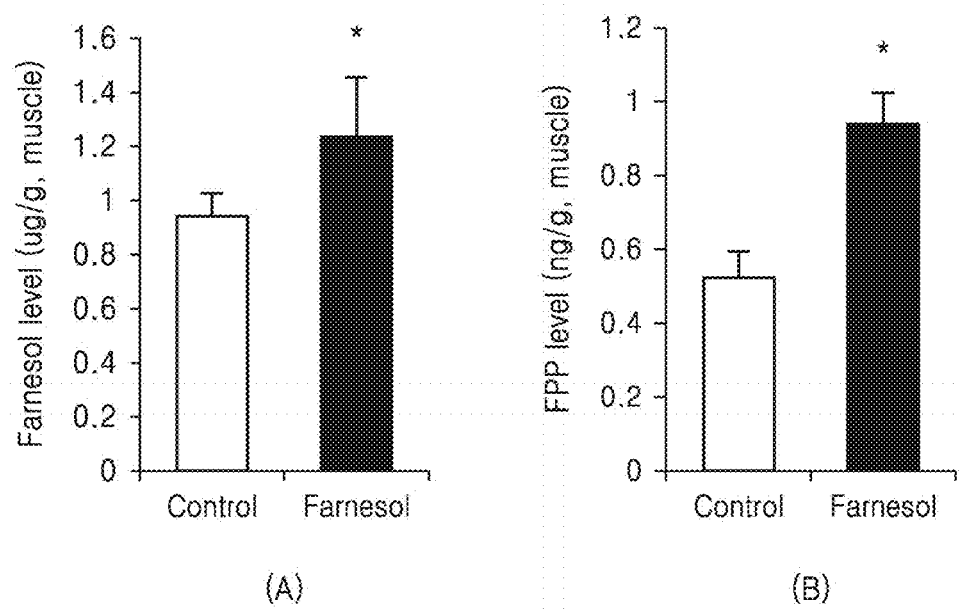
FIG. 1G shows amounts of farnesol (A) and a metabolite thereof, FPP (B) in the extensor digitorum longus muscle cells of farnesol-administered mouse.

FIG. 1G shows amounts of farnesol (A) and a metabolite thereof, FPP (B) in extensor digitorum longus muscle cells of farnesol-administered mouse. As shown in FIG. 1G, in the extensor digitorum longus muscle of a mouse orally administered with farnesol, farnesol is increased to 1.3 times or more, and a metabolite thereof, FPP is increased to 2 times, indicating that farnesol in the feed is successfully transferred to the cells.

Example 3: Effects of Farnesol on Oxidative Muscle and Function of Metabolism in Old Animal 1. Analysis of Oxidative Muscle Capacity and Mitochondrial Activity 22-month-old female mice (weighing 30 g) are fed with a control diet and a farnesol diet for 4 months. That is, 22-month-old mice are fed for 4 months, and then 26-month-old mice are analyzed. A 22-month-old mouse is comparable to a 65-old human, based on a ratio of mouse life expectancy to human life expectancy. As a control group, a 5-month-old young mouse (comparable to a 30-old human) is used.

Figure 2A:
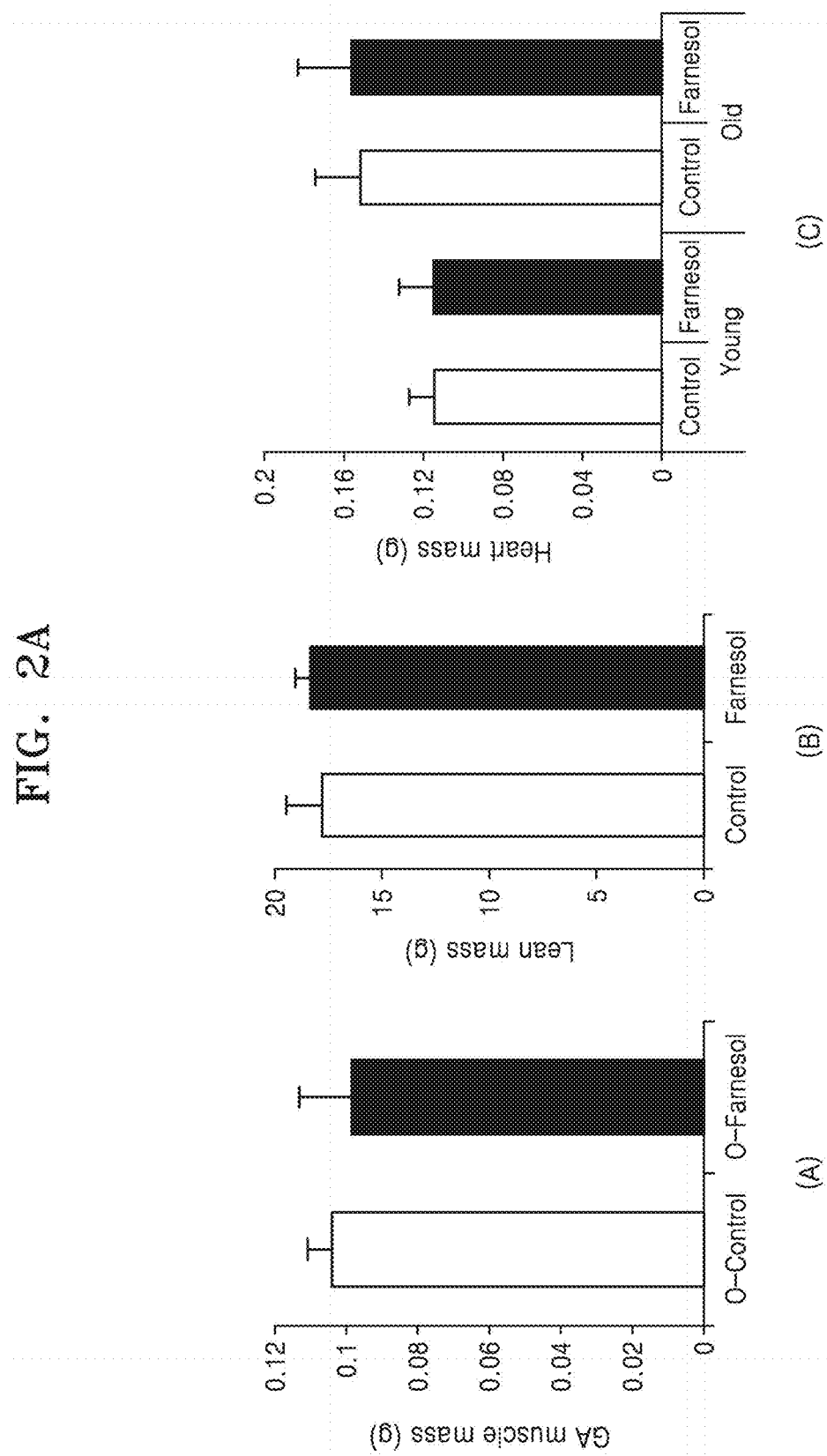
FIG. 2A shows changes in GA muscle mass (A), lean mass (B) and heart mass (C) of mice according to farnesol administration.

FIG. 2a shows changes in GA muscle mass (A), lean mass (B) and heart mass (C) of mice according to farnesol administration. As shown in FIG. 2a, administration of farnesol to old animals hardly changes muscle mass (A: control old animal 0.104 g vs farnesol old animal 0.099 g), lean mass (B: control old animal 15.1 g vs farnesol old animal 15.3 g), and heart mass (C: control young animal 0.116 g vs farnesol old animal 0.115 g, control old animal 0.152 g vs farnesol old animal 0.156 g), indicating that farnesol administration does not cause side effects such as muscular hypertrophy.

Figure 2B:
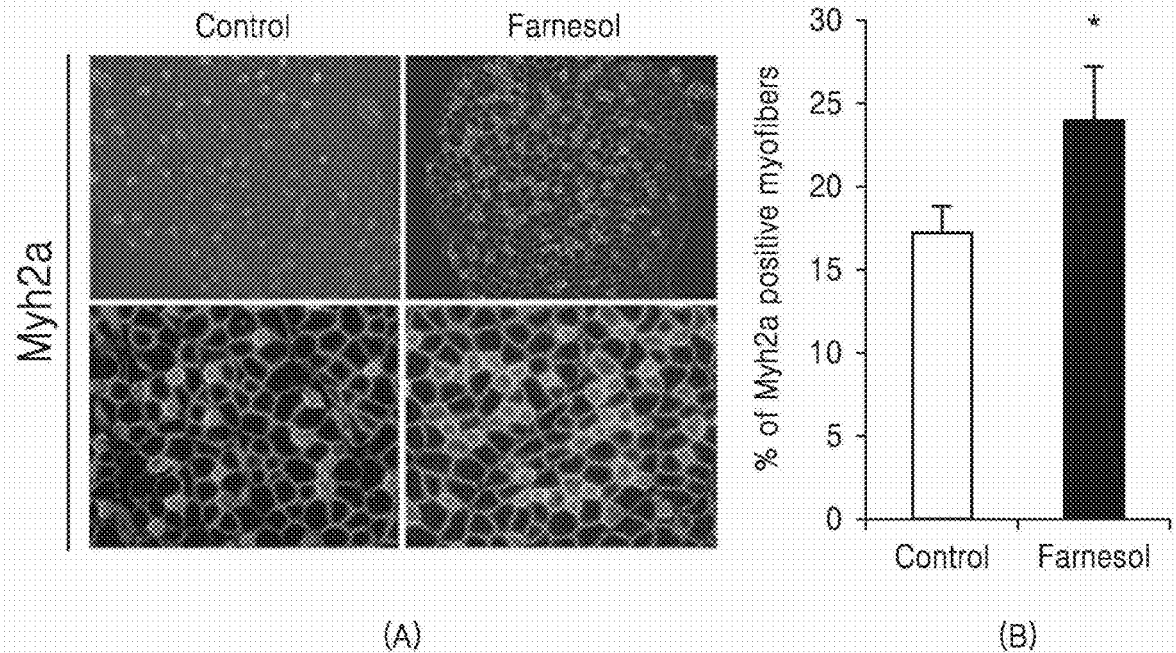
FIG. 2B shows changes in the muscle fiber type in the extensor digitorum longus muscles of old mice administered with farnesol.

Farnesol is administered to mice in the same manner as in Section 3 of Example 2, except that 22-month-old mice are used instead of 5-month-old mice and administration is performed for 4 months instead of 5 weeks, and changes in the skeletal muscle type are examined. FIG. 2b shows changes in the muscle fiber type in the extensor digitorum longus muscles of old mice administered with farnesol. As shown in FIG. 2b, the number of oxidative 2a type muscle fiber is increased to about 1.4 times in the extensor digitorum longus muscles of old mice administered with farnesol, compared to the control group, indicating that farnesol administration also increases oxidative muscle fibers having high mitochondrial activity in old animals.

In FIG. 2B, A is an image showing result of immunohistochemistry of frozen tissue sections for myh2a using anti-myh2a antibody, in which the green color indicates oxidative 2a type muscle fibers stained for myh2a, and the red color indicates total muscle cells stained for laminin, and B shows a percentage of the green-colored cells to the total cells, that is, red-colored cells and green-colored cells in A.

Further, farnesol is administered to mice in the same manner as in Section 4 of Example 2, except that 22-month-old mice are used instead of 5-month-old mice and administration is performed for 4 months instead of 5 weeks, and activity of a mitochondrial enzyme according to farnesol administration is analyzed in the extensor digitorum longus muscles of old mice.

Figure 2C:
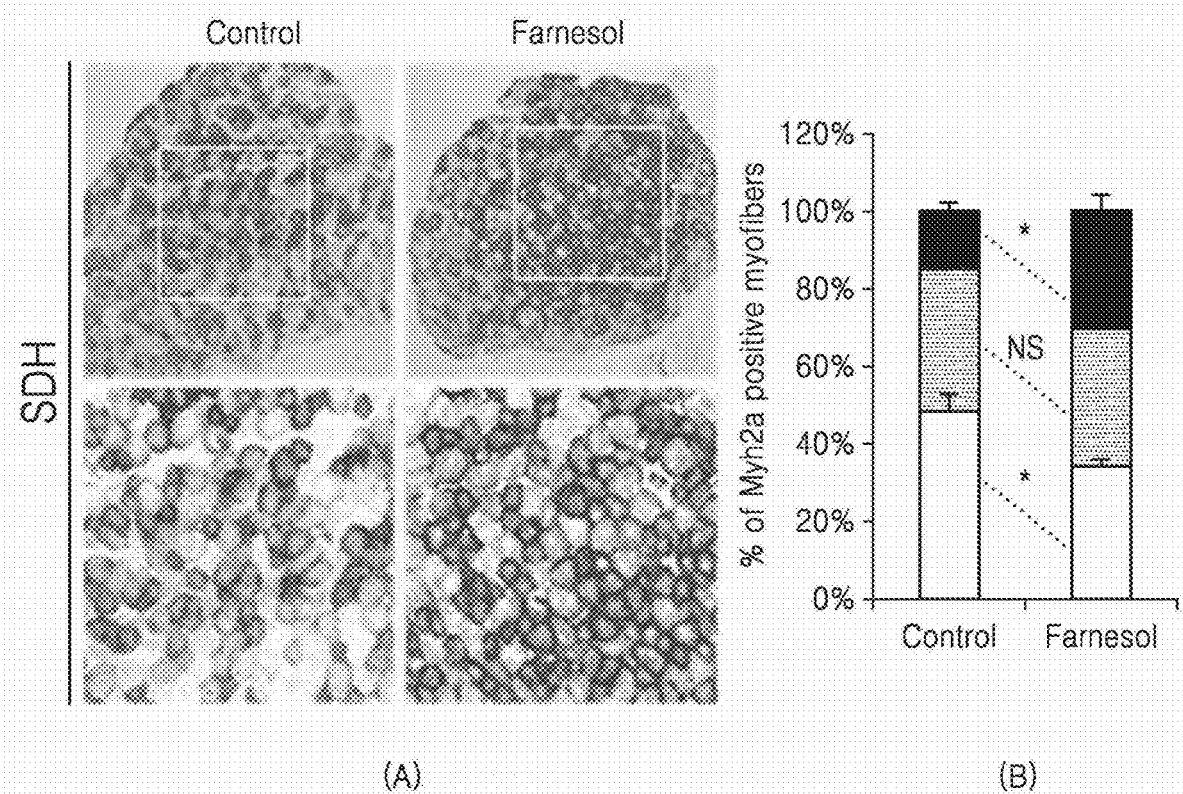
FIG. 2C shows changes of mitochondrial enzyme activity in the extensor digitorum longus muscles of old mice administered with farnesol.

FIG. 2C shows changes of mitochondrial enzyme activity in the extensor digitorum longus muscles of old mice administered with farnesol. In FIG. 2C, A is an image showing result of staining the frozen tissue sections, and B shows a percentage of stained areas of A, which are classified into three intensities of dark, intermediate, and pale. As shown in FIG. 2C, a percentage of the area stained dark is remarkably increased, that is, a percentage of muscle fiber having an increased SDH activity is increased in the extensor digitorum longus muscle of farnesol-administered mouse, compared to a control group, indicating that farnesol administration also activates mitochondrial energy metabolism in muscle fibers of old animals.

2. Analysis of Muscle Strength, Energy Expenditure, Glucose Tolerance, and Fat Mass Ratio 22-month-old female mice (weighing 30 g) are fed with a control diet and a farnesol diet for 4 months. That is, 22-month-old mice are fed for 4 months, and then 26-month-old mice are analyzed. A 22-month-old mouse is comparable to a 65-old human, based on a ratio of mouse life expectancy to human life expectancy. The same mouse is used as a control group, except that it is fed with a diet containing no farnesol. Muscle strength, energy expenditure, glucose tolerance, and fat accumulation of each mouse are evaluated.

Figure 2D:
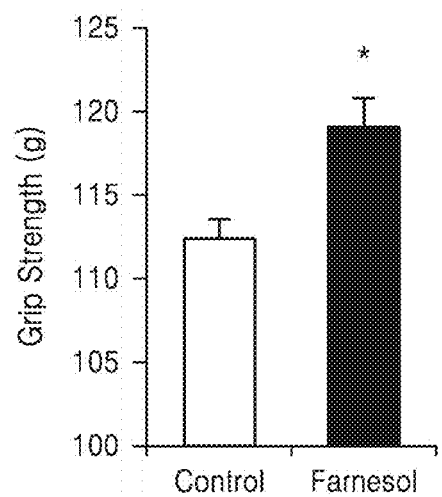
FIG. 2D shows changes in muscle strength (grip strength) of old mice according to farnesol administration.

FIG. 2D shows changes in muscle strength of old mouse according to farnesol administration. To measure grip strength as an index of mouse muscle strength, a grip strength meter (Bioseb) is used.

For measurement of grip strength of mouse, its front paws are allowed to grip the grid, and its tail is then pulled back steadily and horizontally. When the animal releases the grid, the value is used as grip strength. The maximal grip strength values of individual mice are measured 5 times, and mean values are obtained. Results are shown in FIG. 2D. Grip strength is expressed as a force (g, gram) per weight. As shown in FIG. 2D, grip strength is significantly increased in the farnesol-administered old mouse, compared to the negative control old mouse.

Figure 2E:
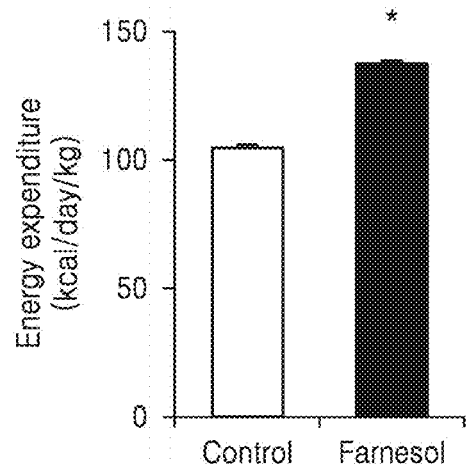
FIG. 2E shows energy expenditure of mice according to farnesol administration.

FIG. 2E shows energy expenditure of mouse according to farnesol administration. To measure energy expenditures of old mice administered with farnesol, mice are bred in a measurement apparatus, Oxylet system (calorimetry apparatus, Panlab Harvard apparatus) for 2 days. A METABOLISM software connected with metabolic measurement modules is used for analysis of energy expenditure. As shown in FIG. 2E, energy expenditures of old mice administered with farnesol are significantly increased, compared to a control old mouse.

Figure 2F:
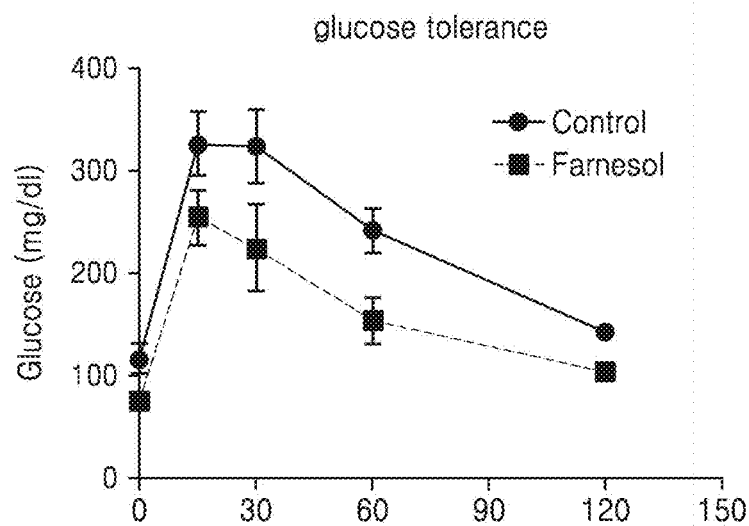
FIG. 2F shows result of a glucose tolerance test of mice according to farnesol administration.
Figure 2G:
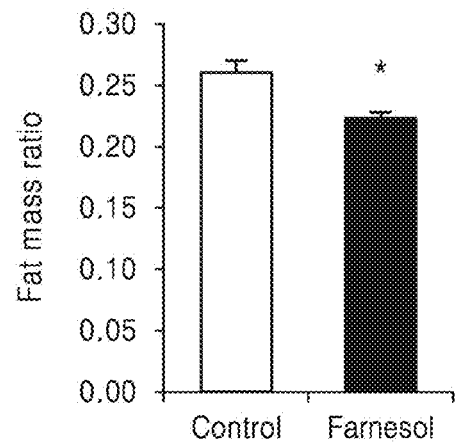
FIG. 2G shows a fat mass ratio of farnesol-administered old mice.

FIG. 2F shows result of a glucose tolerance test of mice according to farnesol administration. To measure glucose tolerance, 1 g of glucose per body weight (kg) is intraperitoneally injected into a control group or a farnesol-administered old mouse, after overnight fast. Blood glucose levels are measured using an Accu-Check glucometer (Roche) before injection of glucose and at 30 minutes, 60 minutes, and 120 minutes after injection of glucose. Glucose tolerance means a capacity of processing injected glucose, and it may be determined by measuring the glucose level. As shown in FIG. 2F, the farnesol-administered old mouse shows a remarkably low blood glucose level, compared to the control group, indicating that the farnesol-administered old mouse has an improved glucose metabolic capacity, compared to the control group FIG. 2G shows a fat mass ratio of farnesol-administered old mouse. The fat mass ratio is determined by dual-energy X-ray absorptiometry (LUNA PIXIMUS, GE Healthcare/LUNA), and measured on combined images after radiation at 40 kV X-ray and 80 kV X-ray four times, respectively. As shown in FIG. 2G, fat mass ratio of old mouse administered with farnesol is significantly decreased, compared to the control group.

Example 4: Effect of Farnesol on Improvement of Muscle Fibrosis

1. Analysis of Muscle Fibrosis-Related Gene Expression

In muscle aging, fibrosis is closely related to a reduction in regenerative capacity and a reduction in quality of muscle. 22-month-old female mice (weighing 30 g) are fed with a control diet or a farnesol-containing diet for 4 months. Other feeding conditions are the same as described in Section 2 of Example 1. Thereafter, expressions of fibrosis-related genes, collagen 1 A1 (Col1 A1), collagen A3(Col A3), TGF-$\beta$, and Timp2 in extensor digitorum longus muscles are analyzed by qRT-PCR (quantitative Real Time-polymerase chain reaction) (primer sets of SEQ ID NOS: 1 and 2, 3 and 4, 5 and 6, 7 and 8 are used).

Figure 3A:
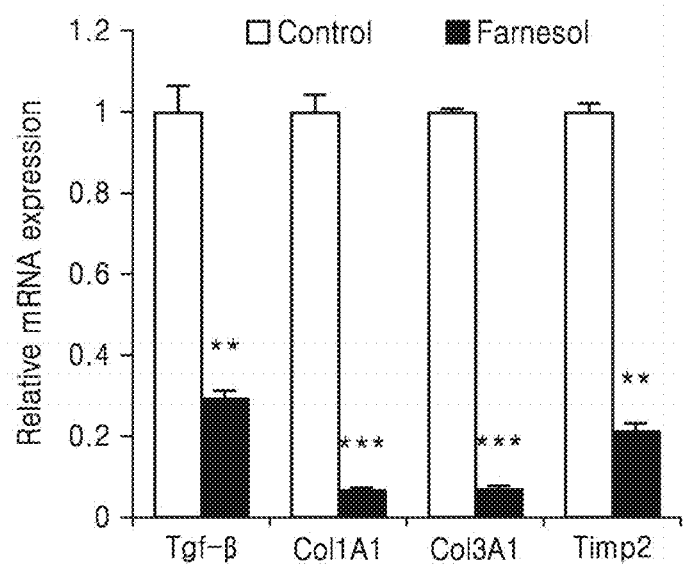
FIG. 3A shows expressions of fibrosis-related genes in extensor digitorum longus muscles of farnesol-administered mice.

FIG. 3A shows expressions of fibrosis-related genes in extensor digitorum longus muscles of farnesol-administered mice. As shown in FIG. 3A, expressions of fibrosis-related genes are remarkably reduced in farnesol-administered mouse, compared to a control group. The vertical axis of FIG. 3A shows relative expression levels of experimental genes in the muscles of farnesol-administered old mouse to expression levels of the genes in a control group mouse, which are measured by qRT-PCR.

2. Effect on Muscle Fibrosis after Induction of Muscle Injury 25-month-old mice are fed with a control diet or a farnesol-containing diet for 2 weeks, and then 2 ul of 10 uM cardiotoxin (CTX) per body weight (g) is directly injected into the muscle to induce muscle injury. After 4 days, muscles are frozen and sectioned, followed by histological staining.

Figure 3B:
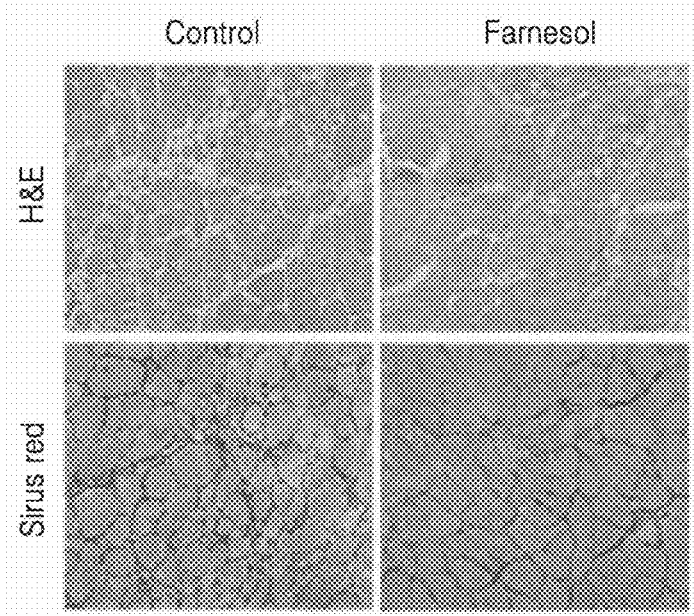
FIG. 3B shows results of histological staining of injured tibialis anterior muscles (TA) of old animals.

FIG. 3B shows results of histological staining of injured tibialis anterior muscles (TA) of old animals. Hematoxylin and eosin (H&E) staining and sirus red staining are used in histological staining. Because muscle fibrosis is reduced and muscle regeneration is active at 4 days after muscle injury, effect of farnesol administration may be determined by histological staining. H&E staining is performed to examine structural recovery of injury, and sirus red staining is performed to examine the presence of fibrosis. As shown in FIG. 3B, H&E staining shows that the size of muscle fibers stained red is increased in an experimental group compared to a control group. Further, sirus red staining shows that a percentage of blue and red stained muscle fibers is remarkably reduced in the experimental group compared to the control group. That is, the control old animal has more thicker fibrosis regions located between the fibers than the experimental old animal treated with farnesol. Therefore, this experiment shows that the farnesol-treated old mouse has a widespread regenerative region and a narrow fibrotic area, compared to the control group.

Figure 3C:
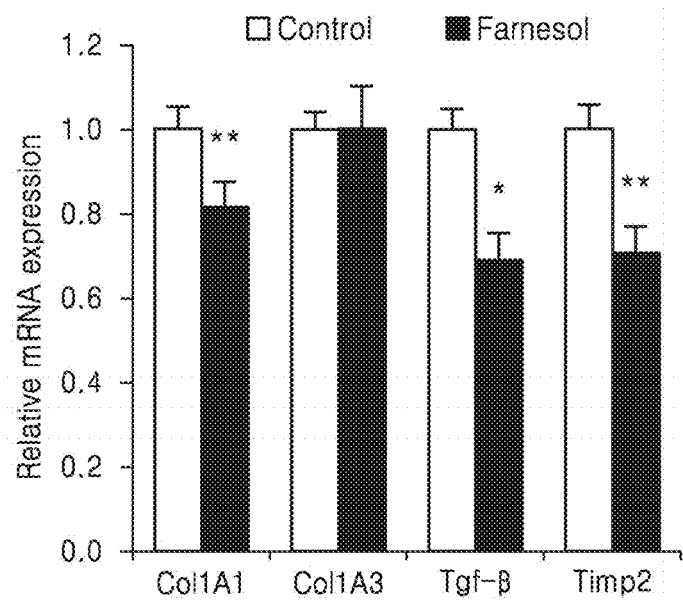
FIG. 3C shows expressions of fibrosis-related genes in the injured tibialis anterior muscle of old mouse.

In addition, expressions of fibrosis-related genes, TGF-$\beta$, Col A1, collagen A3, and Timp2 in tibialis anterior muscle are analyzed by qRT-PCR as described above. FIG. 3C shows expressions of fibrosis-related genes in the injured tibialis anterior muscle of old mouse. As shown in FIG. 3C, expressions of fibrosis-related genes are significantly reduced in the farnesol-treated old mouse, compared to a control group.

Results of Example 4 show that farnesol protects muscles from age-related alteration and fibrosis.

Example 5: Identification of Target Factors of Farnesol in Muscle

1. Relationship Between Farnesol and PGC-1α and PARIS Expressions

PGC-1α transcriptional regulation is known to be associated with activation of AMP-activated protein kinase (AMPK) and p38 mitogen-activated protein kinase (p38 MAPK). It is examined whether farnesol increases PGC-1α expression via AMPK and p38 MAPK.

Figure 4A:
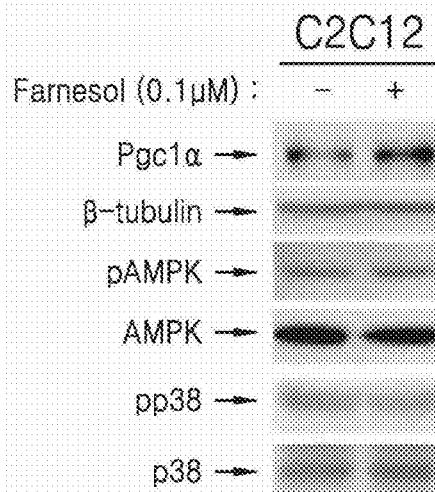
FIG. 4A shows immunoblot analysis of farnesol-treated C2C12 myoblasts.

FIG. 4A shows immunoblot analysis of farnesol-treated C2C12 myoblasts. The C2C12 myoblasts are cultured in DMEM containing 2% horse serum and 0.1 µM farnesol dissolved in DMSO for 48 hours. A control group is cultured in the same manner as above, except that only DMSO is added. Other culture conditions and immunoblot procedure are the same as those described in Section 1 of Example 2. PGC-1α, pAMPK, pp38 and basal forms thereof are subjected to immunoblotting. As shown in FIG. 4A, farnesol does not affect pAMPK and pp38 levels.

Figure 4B:
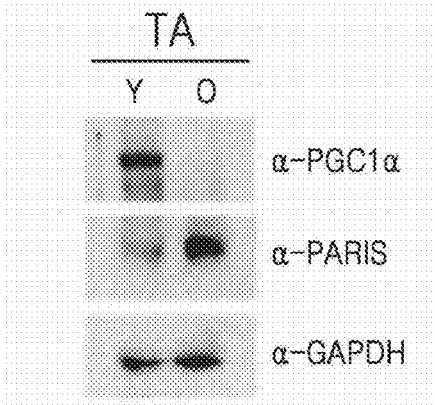
FIG. 4B shows immunoblot analysis of PGC-1α and PARIS in tibialis anterior muscles of a young mouse (4-month-old, body weight of 22 g) and an old mouse (24-month-old, body weight of 30 g)

FIG. 4B shows immunoblot analysis of PGC-1α and PARIS in tibialis anterior muscles of a young mouse (4-month-old, body weight of 22 g) and an old mouse (24-month-old, body weight of 30 g). PGC-1α and PARIS protein levels are examined in the 4-month-old mouse (Y) and 24-month-old mouse (O). As shown in FIG. 4B, PGC-1α expression is decreased, but PARIS expression is increased in the old mouse, compared to the young mouse.

Figure 4C:
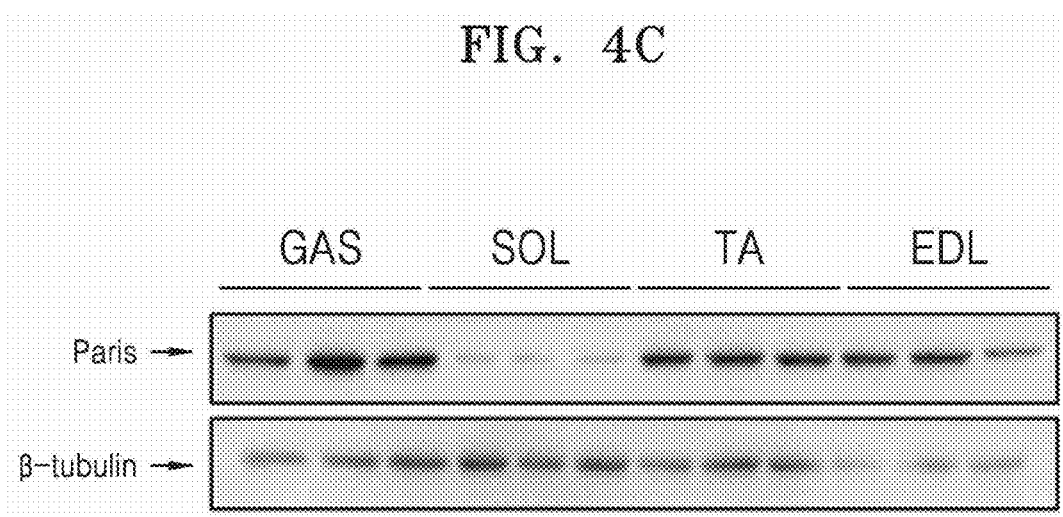
FIG. 4C shows immunoblot analysis of PARIS in the lower limb muscle of a 4-month-old mouse (female, body weight of 22 g)

FIG. 4C shows immunoblot analysis of PARIS in the lower limb muscle of a 4-month-old mouse (female, body weight of 22 g). GAS indicates gastrocnemius muscle, SOL indicates soleus muscle, TA indicates tibialis anterior muscle, and EDL indicates extensor digitorum longus muscle. As shown in FIG. 4C, PARIS shows the lowest expression in soleus muscles (SOL) largely made up of oxidative fibers and expressing PGC-1α in the highest level. Other lower limb muscles are made up of different percentages of oxidative and glycolytic fibers.

Figure 4D:
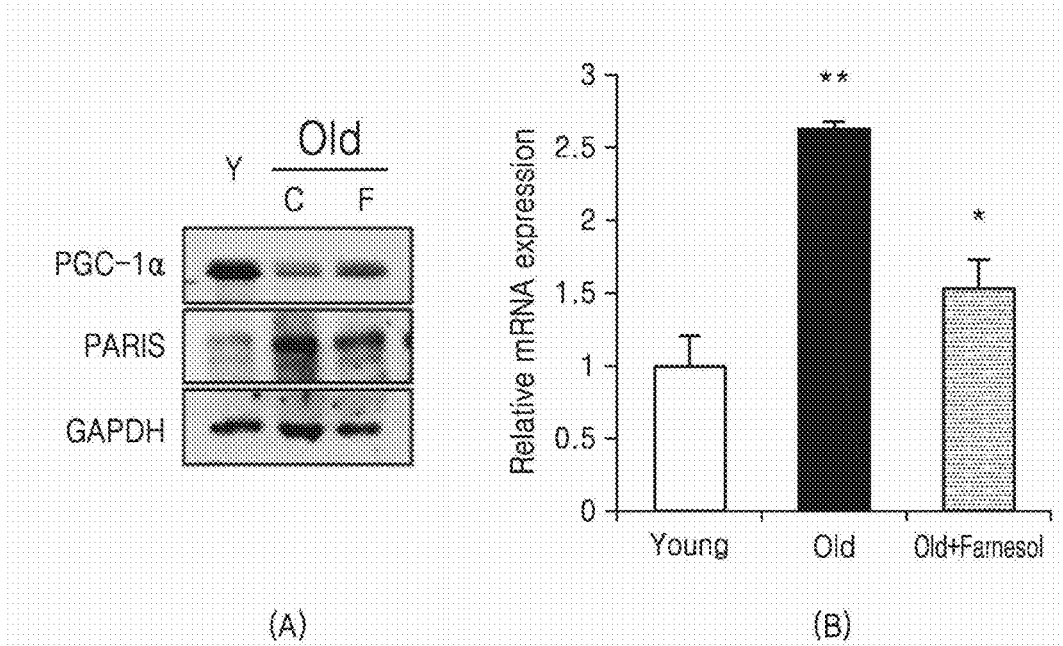
FIG. 4D shows protein expression levels (A) and transcriptional levels of PARIS (B) in extensor digitorum longus muscles of a 4-month-old young mouse (female, 22 g), a 24-month-old mouse (female, 22 g) and a farnesol-administered 24-month-old mouse.

FIG. 4D shows protein expression levels (A) and transcriptional levels of PARIS (B) in extensor digitorum longus muscles of a 4-month-old young mouse (female, 22 g), a 24-month-old mouse (female, 22 g) and a farnesol-administered 24-month-old mouse. As shown in FIG. 4d, the protein expression level and transcriptional level of PARIS in extensor digitorum longus muscles are significantly increased in the old mouse, compared to the young mouse. The protein expression level and transcriptional level of PARIS are remarkably decreased in the old mouse administered with farnesol for 5 weeks ('F' in A and 'Old+Farnesol' in B), compared to the old mouse administered with no farnesol ('C' in A and 'Old' in B), indicating that farnesol decreases the transcriptional level of PARIS which increases with aging.

2. Effect of Farnesol on PARIS-Overexpressing Myoblasts

In C2C12 myoblasts, a PARIS gene expression vector (pCMV-Tag2A, Stratagene) is transiently expressed, followed by immunoblotting and immunostaining analysis. PARIS gene is a full length cDNA of human PARIS gene having a nucleotide sequence of SEQ ID NO: 9.

Figure 4E:
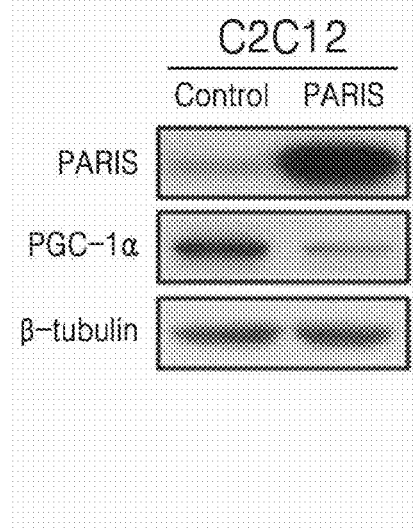
FIG. 4E shows PARIS and PGC-1α protein expressions in PARIS gene-overexpressing myoblasts.

FIG. 4E shows PARIS and PGC-1α protein expressions in PARIS gene-overexpressing myoblasts. As shown in FIG. 4E, PARIS-overexpressing C2C12 cells show a significant decrease in PGC-1α expression, compared to a control group.

Figure 4F:
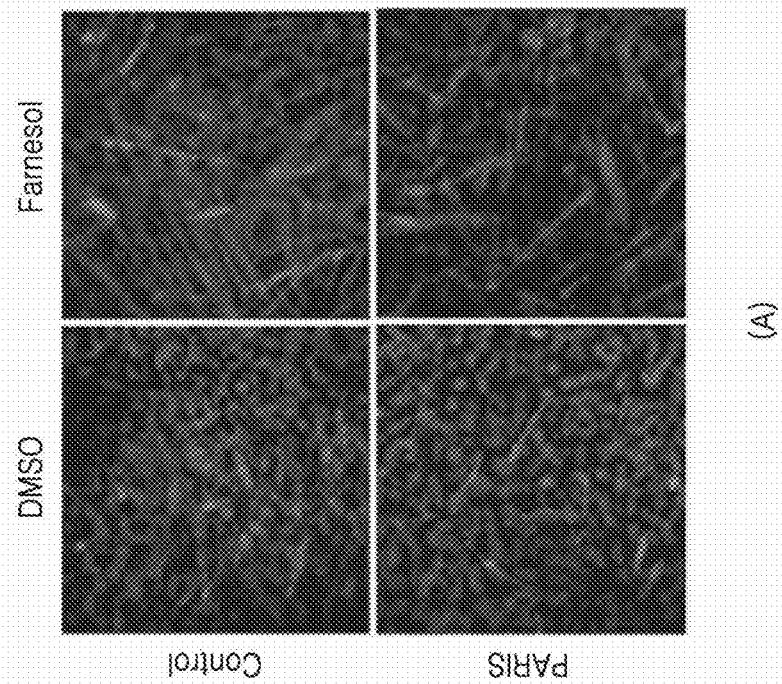
FIG. 4F shows effect of farnesol on differentiation of PARIS-overexpressing myoblasts.

FIG. 4F shows effect of farnesol on differentiation of PARIS-overexpressing myoblasts. After induction of differentiation of PARIS-overexpressing C2C12 cells for 3 days, immunostaining for Myh expression is performed. To induce the differentiation, cells are cultured in DMEM containing 2% horse serum and 0.1 µM farnesol dissolved in DMSO for 48 hours. A control group is cultured in the same manner as above, except that only DMSO is added. Other culture conditions are the same as those described in Section 1 of Example 2.

As shown in panel (A) of FIG. 4F, PARIS overexpression decreases Myh-positive myotube formation, and reduced myotube formation is recovered by farnesol treatment. In (A) of FIG. 4F, Control represents myoblasts introduced with no PARIS gene expression vector, and 'PARIS' represents myoblasts introduced with a PARIS gene expression vector. In these experiments, blue color staining indicates nuclei, and red color staining indicates stained myh and also myotubes. The colors are not shown in panel (A) of FIG. 4F, but the difference in the relative amount of red color stained area is quantified in panel (B) of FIG. 4F, wherein pCMV represents the control myoblasts without a PARIS gene expression vector. From panel (B) of FIG. 4F, it can be seen that the red color stained area of 'PARIS' cell treated with DMSO is smaller than that of 'CONTROL' cell treated with DMSO, and the red color stained area of 'PARIS' cell treated with Farnesol is smaller than that of 'CONTROL' cell treated with Farnesol. Also, the red color stained area of 'CONTROL' cell treated with DMSO is smaller than that of 'CONTROL' cell treated with Farnesol, and the red color stained area of 'PARIS' cell treated with DMSO is smaller than that of 'PARIS' cell treated with Farnesol.

3. Effect of Farnesol on PARIS-Overexpressing Muscles

Control-GFP adenovirus and PARIS-GFP adenovirus are injected into the tibialis anterior muscles of 22-month-old mice (female, body weight of 30 g), respectively. The old mice are fed with a predetermined diet, and 4 days later, muscles are collected and subjected to histological staining and qRT-PCR. For PARIS overexpression, human full-length PARIS cDNA (IMAGE: 30347892; Open Biosystems) (SEQ ID NO:9) is introduced into BamH1 and EcoR1 restriction sites of a viral vector, AAV/CBA-WPRE-bGHpA (containing chicken beta-actin (CBA) promoter and woodchuck hepatitis virus post-transcriptional-regulatory element (WPRE), and bovine growth hormone polyadenylation signal sequence) to prepare a full-length PARIS cDNA-containing AAV/CBA-WPRE-bGHpA vector, and this vector is introduced into the adenovirus-introduced cells. A high titer adenovirus (Adeno-associated Virus, AAV) is a viral vector manufactured by Viral Vector Core Facility (University of Iowa Carver College). Virus transduction efficiency is evaluated by GFP fluorescence. To evaluate PARIS overexpression and administration effect of farnesol, frozen sections of tibialis anterior muscles are stained for SDH enzyme activity.

Figure 4G:
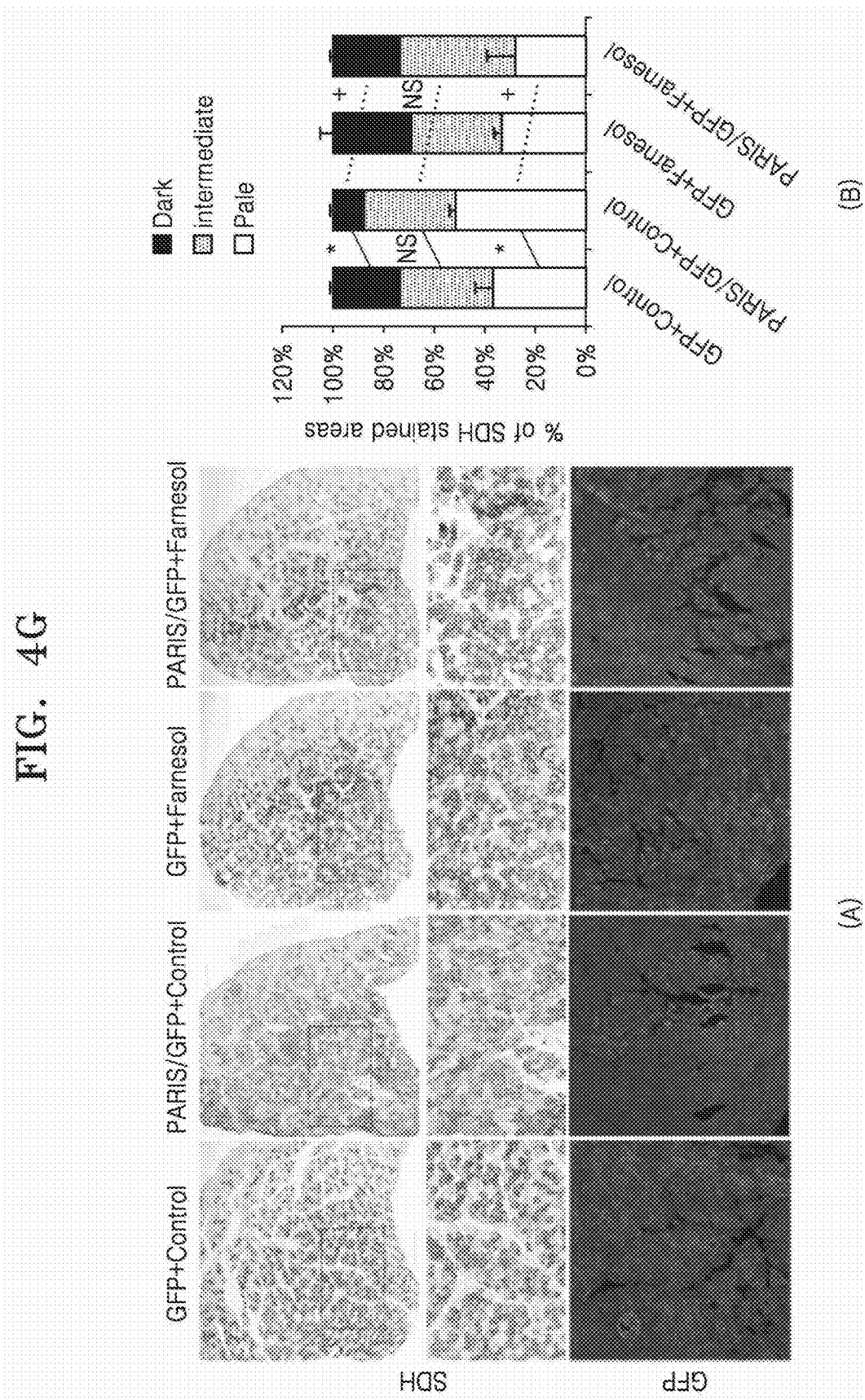
FIG. 4G shows effect of farnesol on PARIS-overexpressing muscles.

FIG. 4G shows effect of farnesol on PARIS-overexpressing muscles. As shown in FIG. 4G, GFP expression is detected in the majority of muscle fibers, and the tibialis anterior muscles transduced with PARIS by adenovirus show strong SDH staining with muscle fiber reduction, indicating that PARIS overexpression reduces oxidative muscle metabolism. Further, similar to the result in C2C12 myoblast models, an oxidative metabolism reduced by PARIS overexpression is also recovered by farnesol treatment in animal models. In FIG. 4G, A shows results of staining frozen tissue sections for SDH enzyme activity (upper 2 rows) and GFP fluorescence (the bottom image), in which green indicates GFP fluorescence, and B shows a percentage of stained areas of A, which are classified into three intensities of dark, intermediate, and pale. The first row shows low-magnification images of SDH enzyme activity staining, and the second row shows magnification of the black boxes. There are 4 groups in figure: a control group is represented by GFP+control, PARIS overexpression is represented by PARIS/GFP+control, farnesol-administered control group is represented by GFP+Farnesol, and farnesol-administered PARIS overexpression is represented by PARIS/GFP+Farnesol.

Example 6: Mechanism of Increased PGC-1α Expression and Oxidative Metabolism by Farnesol Target Factor 1. Relationship Between Farnesol and Farnesylation of PARIS C2C12 cells are cultured in the presence of farnesol, and cell lysate is subjected to immunoprecipitation. As an experimental group, C2C12 cells are cultured in the presence of 10 uM farnesol for 24 hours, and also cultured in the differentiation medium described in Section 2 of Example 1 for 24 hours by adding 10 uM farnesol according to a culturing schedule, that is, at 0 day, 1 day, 2 days, 3 days, and 4 days (hereinafter, also referred to as 'D0, D1, D2, D3 and D4' or 'D0-D04'). Next, a cell lysis buffer (20 mM Tris-HCl, pH 8, 150 mM NaCl, 1% Triton X, Proteinase Inhibitor) is added to the harvested cells, and cell lysis is allowed under refrigeration for 60 minutes, followed by centrifugation at 13,000 rpm for 20 minutes. A supernatant is removed by 50 uL of protein A/G-agarose in advance, and a target protein antibody is reacted for 12 hours or longer. The resultant is mixed with protein A/G-agarose beads, and stirred for 1 hour. The beads are washed with a cold lysis buffer at a low concentration three times to remove abnormal protein binding. The obtained sample is mixed with a 2×SDS sample buffer (0.125 M Tris-HCl (pH 6.8), 4% SDS, 10% β-mercaptoethanol, 18% glycerol, and 0.1% Bromophenol Blue), and then electrophoresed on 8% SDS-PAGE. The sample is transferred onto a PVDF membrane, and then incubated in a blocking buffer containing 5% skim milk for 1 hour. individual protein-specific rabbit antibodies diluted in 5% BSA (hereinafter, referred to as 'primary antibody') are reacted with the membrane at 4° C. for 12 hours, and then washed with a wash buffer for 5 minutes three times. An anti-rabbit antibody (hereinafter, referred to as 'secondary antibody') is diluted in the blocking buffer, and reacted with the membrane at room temperature for 1 hour. The membrane is washed with the wash buffer for 5 minutes three times, and exposed to an X-ray film using an ECL reagent (Roche) to examine protein expression levels.

Figure 5A:
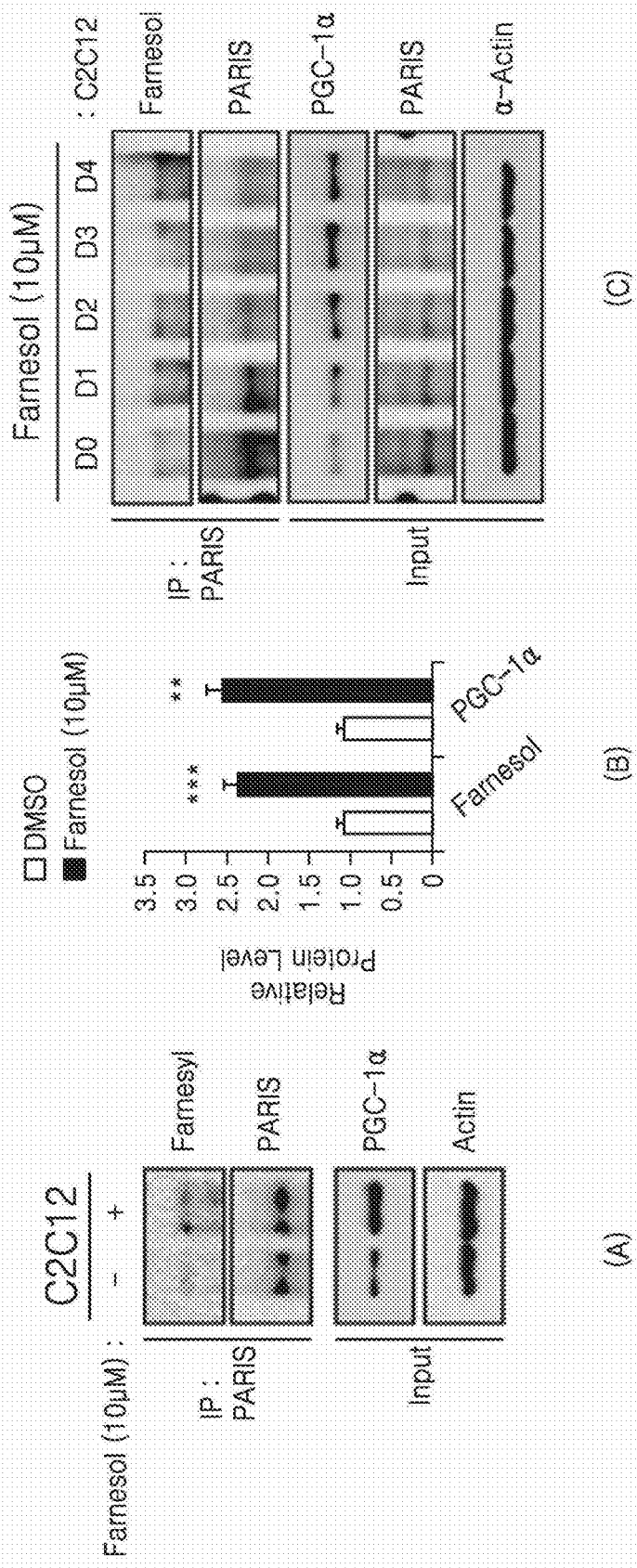
FIG. 5A shows immunoprecipitation analysis for PARIS farnesylation in myoblasts.

FIG. 5A shows immunoprecipitation analysis for PARIS farnesylation in myoblasts. As shown in FIG. 5A, PGC-1α protein level is increased with increasing PARIS farnesylation. PGC-1α expression is increased in 10 uM farnesol-treated myoblasts, compared to a control group, and PARIS antibody is used to perform immunoprecipitation and anti-Farnesyl antibody is used to measure the changes (A). (B) is a quantification graph of the expression levels of (A). In (C) of FIG. 5A, when myoblasts are cultured in the presence of 10 uM farnesol for 0 day, 1 day, 2 days, 3 days, and 4 days (hereinafter, 'D0, D1, D2, D3 and D4'), PGC-1α expression is increased with endogenous PARIS farnesylation, and farnesol treatment further increases farnesylated PARIS level.

To examine whether farnesol increases PARIS farnesylation in muscles, immunoprecipitation of PARIS is performed in tibialis anterior muscles of 4-month-old mice (female, 22 g) fed with farnesol for a predetermined period, that is, 0, 1, 2, and 3 days. The tibialis anterior muscles which are removed from the mice fed with farnesol are mixed with a lysis buffer (10 mM Tris-HCl, pH 7.4, 150 mM NaCl, 5 mM EDTA, 1% triton X-100, 10 mM Na-β-glycerophosphate, and Complete Protease Inhibitor Mixture (Roche)), and homogenized using a Diax 900 tissue homogenizer. The tissues are left under refrigeration for 30 minutes, and centrifuged at 52,000 rpm for 20 minutes. A supernatant is used for immunoprecipitation.

Figure 5B:
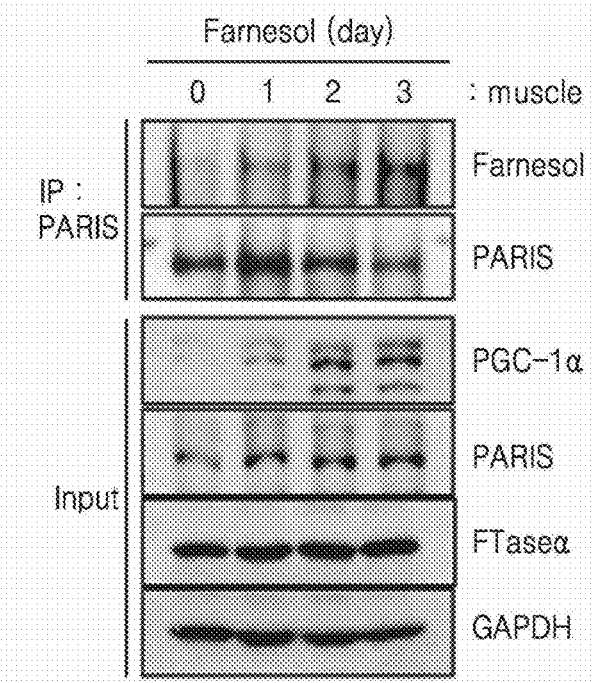
FIG. 5B shows immunoprecipitation analysis for PARIS in muscles.

FIG. 5B shows immunoprecipitation analysis for PARIS in muscles. As shown in FIG. 5B, endogenous PARIS farnesylation occurs, and farnesol treatment further increases farnesylated PARIS level. There is a correlation between increased farnesylated PARIS level and increased PGC-1α level.

2. Identification of Farnesylation Site of PARIS

Figure 5C:
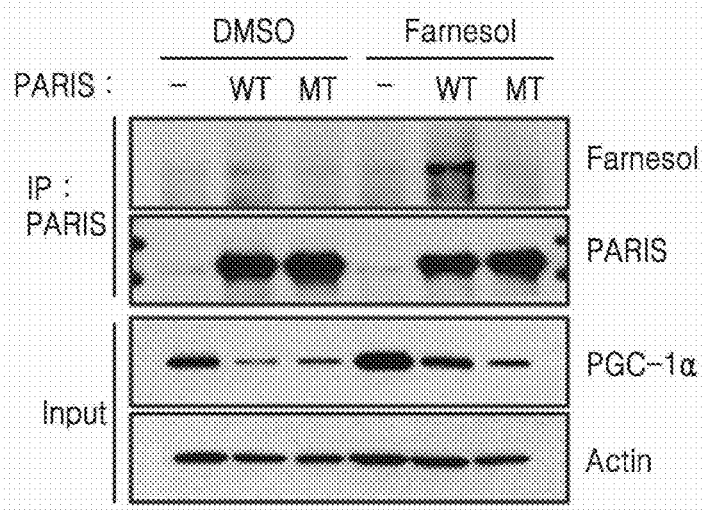
FIG. 5C shows result of identifying major farnesylation sites of PARIS.

FIG. 5C shows result of identifying major farnesylation sites of PARIS.

To examine whether cysteine residues of CGLS sequence (631-634) of an amino acid sequence (SEQ ID NO: 11) of human PARIS are farnesylation sites, a FLAG-PARIS wild-type (WT) gene or a FLAG-PARIS C631S mutant (hereinafter, referred to as "MT") gene is introduced into C2C12 myoblasts in the presence of DMSO or 0.1 uM farnesol, and the gene is expressed in C2C12 myoblasts by culturing them in DMEM containing 10% FBS for 24 hours. Immunoprecipitation and promoter activity analysis of a cell lysate are performed. The site of amino acid sequence (SEQ ID NO: 10) of mouse PARIS corresponding to CGLS sequence (631-634) of the amino acid sequence (SEQ ID NO: 11) of human PARIS is residues at positions 638-641. This CGLS sequence is conserved in mammals as well as humans and mice, and thus C of CGLS which is located at the C-terminus is a farnesylation site regardless of the length of the sequence.

Human full length PARIS cDNA (IMAGE: 30347892; Open Biosystems) (SEQ ID NO: 9) is cloned into BamH1 and EcoR1 restriction sites of a mammalian gene expression vector, pCMV-Tag2A (Stratagene). The pCMV-Tag2A vector is a plasmid-derived mammalian expression vector for tagging proteins with an N-terminal FLAG epitope. A QuikChange site-directed mutagenesis kit (Stratagene) is used to prepare pCMV-PARIS C631S, in which a PARIS C631S gene mutant obtained by substituting serine for the cysteine residue at position 631 of human PARIS is cloned into BamHI and EcoRI restriction sites of pCMV-Tag2A (Stratagene). After preparation of the mutant gene, the gene is introduced into pCMV to prepare an overexpression vector. To prepare the PARIS C631S gene, a pair of primers (SEQ ID NOS: 12 and 13) is used. Thereafter, a nucleotide sequence of the PARIS C631S gene thus prepared is confirmed by automated DNA sequencing.

FIG. 5C shows immunoprecipitation of the PARIS C631S mutant. As shown in FIG. 5C, PARIS WT is farnesylated, and this farnesylation is increased by farnesol treatment. In the case of PARIS C631S mutant, no farnesylation occurs. Farnesol treatment increases farnesylation of PARIS WT, which is consistent with PGC-1α increase. In the case of PARIS C631S mutant, farnesol does not affect PGC-1α level. In FIG. 5C, – represents C2C12 myoblasts introduced with no PARIS gene, and WT and MT represent C2C12 myoblasts introduced with the wild-type PARIS gene and the mutant PARIS gene, that is, PARIS C631S gene, respectively. Further, Farnesyl, PARIS, PGC-1α, and α-Actin represent immunoprecipitations and expression levels of Farnesyl-PARIS, PARIS, PGC-1α and α-Actin, respectively. Input represents expression levels in non-immunoprecipitated myoblasts.

Additionally, it is examined whether the presence of farnesol affects farnesylation of PARIS protein in skeletal muscles. To this end, the FLAG-PARIS wild-type (WT) gene or the FLAG-PARIS C631S mutant (hereinafter, referred to as MT) gene is overexpressed in C2C12 myoblasts, and then farnesol is treated thereto, followed by measurement of differentiation. The muscles of mice are introduced with AAV-GFP, AAV-PARIS WT or AAV-PARIS C631S viral vector, and mice are bred by feeding with farnesol, followed by measurement of mitochondrial enzyme activity.

Figure 5D:
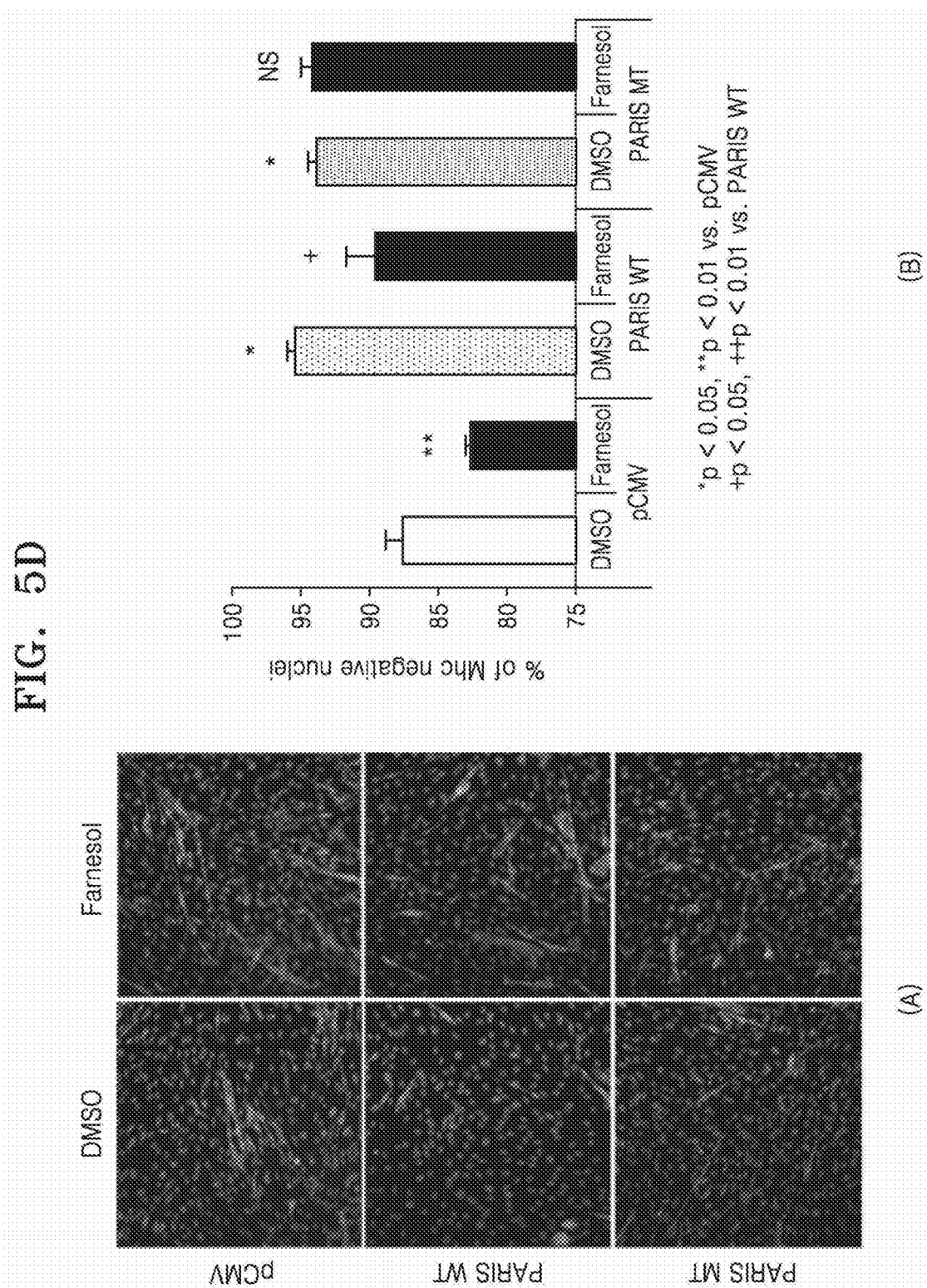
FIG. 5D shows effect of farnesol on PARIS WT gene- or PARIS C631S gene-introduced C2C12 myoblasts.

FIG. 5D shows effect of farnesol on PARIS WT gene- or PARIS C631S gene-introduced C2C12 myoblasts. In FIG. 5D, C2C12 myoblasts are introduced with FLAG-PARIS wild-type (WT) gene or FLAG-PARIS C631S mutant (hereinafter, referred to as "MT") gene, and cultured in the presence of 0.1 M farnesol in DMEM containing 10% FBS for 24 hours, followed by measurement of muscle differentiation and mitochondrial enzyme activity. Muscle differentiation is examined by immunostaining using a muscle differentiation marker, Mhc. In FIG. 5D, A shows DAPI-staining, in which the blue color represents nuclei and the red color represents Myh-positive myotube formation. B shows a percentage of Mhc-negative nuclei in each experimental sample. The percentage of Mhc-negative nuclei indicates the cells showing no formation of red-colored myotube among the nucleus-stained myoblasts of A.

As shown in FIG. 5D, the presence of farnesol significantly decreases the percentage of Mhc-negative nuclei of C2C12 myoblasts introduced with FLAG-PARIS WT gene, but does not significantly decrease the percentage of Mhc-negative nuclei of C2C12 myoblasts introduced with FLAG-PARIS MT, namely, FLAG-PARIS C631S gene (see B of FIG. 5D), indicating that the presence of farnesol inhibits a reduction in differentiation of FLAG-PARIS WT gene-introduced C2C12 myoblasts into muscle cells, that is, a reduction in muscle fiber production, but not in FLAG-PARIS C631S gene-introduced C2C12 myoblasts.

Figure 5E:
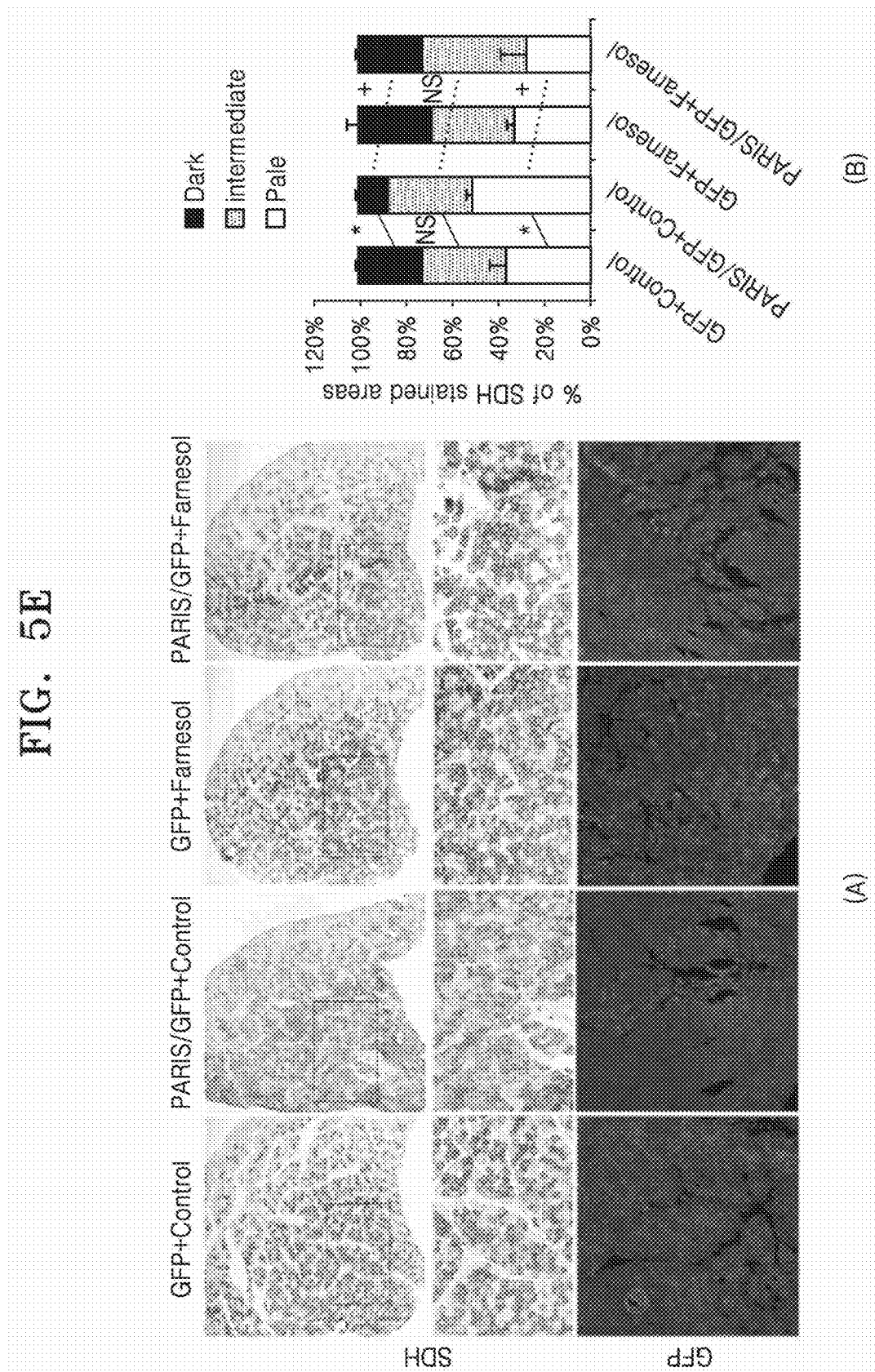
FIG. 5E shows result of measuring mitochondrial enzyme activity after introducing an AAV-GFP, AAV-PARIS WT or AAV-PARIS C631S viral vector into the mouse muscles and feeding the mice with farnesol.

FIG. 5E shows result of measuring mitochondrial enzyme activity after introducing an AAV-GFP, AAV-PARIS WT or AAV-PARIS C631S viral vector into the mouse muscles and feeding the mice with farnesol.

5-month-old C57BL/6 male mice (body weight of 22 g) are fed with a control diet or a farnesol-containing diet for 1 week, and then AAV-GFP, AAV-PARIS WT or AAV-PARIS C631S virus is injected into tibialis anterior muscles. Feeding conditions, not mentioned, are the same as in Section 2 of Example 2. After 4 days, the muscles are collected and histological staining is performed to analyze mitochondrial enzyme activity. The staining is performed by SDH enzyme activity staining. Viral transduction efficiency is evaluated by GFP fluorescence.

As shown in FIG. 5E, administration of farnesol to mouse inhibits a reduction in the mitochondrial enzyme activity of AAV-PARIS WT-introduced muscles, but not in AAV-PARIS C631S-introduced muscles. In FIG. 5E, upper 2 rows of A show SDH staining results, and the third row shows GFP fluorescence, and B shows a percentage of stained SDH of A, which are classified into three intensities of dark, intermediate, and pale. NS (Non-Significant) stands for not statistically significant, indicating that there is no change by farnesol treatment.

Results of Example 6 suggest that farnesol treatment increases PARIS farnesylation to increase PGC-1α expression and oxidative metabolism in muscles.

Example 7: Identification of PARIS as a Target Factor of Muscle Improvement by Exercise 1. PGC-1α Induction Test In PGC-1α induction by PARIS-farnesylation, effect of exercise is evaluated.

To analyze effect of short-term exercise, 7-month-old mouse (female, body weight of 28 g) and 22-month-old mouse (female, body weight of 30 g) are exercised on a treadmill. Prior to excise on a treadmill, they are adapted for 5 minutes at a speed of 7 meters per minute for 5 days. This treadmill exercise program is a short-term aerobic exercise program performed at an incline of 10 grade and at a speed of 9 meters per minute for 30 minutes for 5 days. Immunoblotting analysis of PGC-1α and PARIS in gastrocnemius muscles of the exercised 4-month-old mouse and 22-month-old mouse is performed.

Figure 6A:
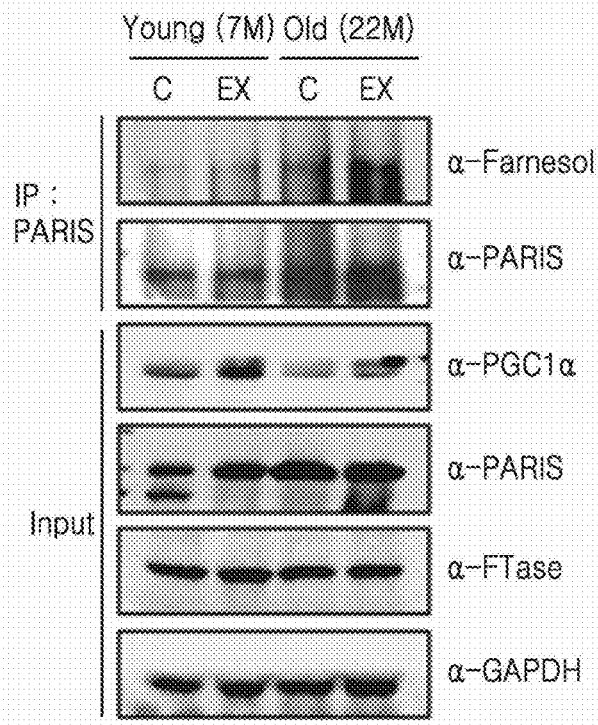
FIG. 6A shows PGC-1α expression and PARIS-farnesylation levels in the muscle of short-term exercised old mouse.

FIG. 6A shows PGC-1α expression and PARIS-farnesylation levels in the muscle of short-term exercised old mouse. As shown in FIG. 6A, the muscle of the short-term exercised old mouse shows a decrease in PARIS-farnesylation and an increase in PGC-1α expression without changes in the PARIS level. In FIG. 6A, C represents a non-exercised control group, and Ex represents a short-term exercised experimental group.

To analyze effect of long-term exercise, the young mouse and old mouse are exercised on a treadmill for 5 weeks. Immunoblotting analysis of PGC-1α and PARIS in gastrocnemius muscles of the exercised mice is performed. The mice are adapted for 1 week at a very low speed, and then exercised on the treadmill at a speed of 9 meters per minute and at an incline of 10 grade for 30 minutes every day for 5 weeks.

Figure 6B:
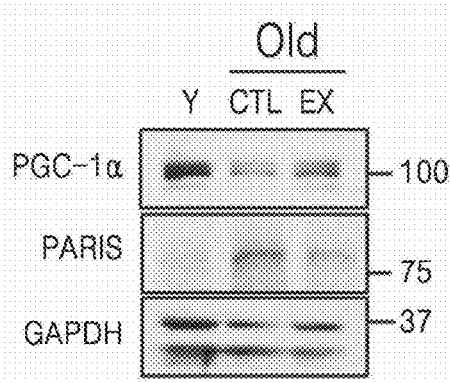
FIG. 6B shows PGC-1α and PARIS expression levels in the muscle of long-term exercised old mouse.

FIG. 6B shows PGC-1α and PARIS expression levels in the muscle of long-term exercised old mouse. As shown in FIG. 6B, the muscle of the long-term exercised old mouse shows an increase in PGC-1α level and a decrease in PARIS level. In FIG. 6A, Y represents a young mouse, CTL represents a non-exercised old mouse control group, and Ex represents a mid-term exercised old mouse experimental group.

2. PGC-1α Inhibition Test

FIGS. 6c through 6f show effect of farnesol in a PGC-1α-inhibited model.

To prepare the PGC-1α-inhibited model, 3-month-old mouse (female, body weight of 20 g) is fed with high fat diet, in which fat is increased to 60%, compared to a negative control group, for 5 days (short-term effect) or 3 months (long-term effect). The negative control group is fed with a general diet. Farnesol is mixed in the high fat diet at a content of 0.5% (weight of farnesol/weight of diet). A positive control group is fed with high fat diet containing a type II diabetes drug, metformin at a content of 0.5% (weight of metformin/weight of diet). Mice are fed with the general diet, the high fat diet, and the high fat diet containing farnesol or metformin for 3 months, and then hind limbs are removed to analyze muscle differentiation and mitochondrial enzyme activity.

Figure 6C:
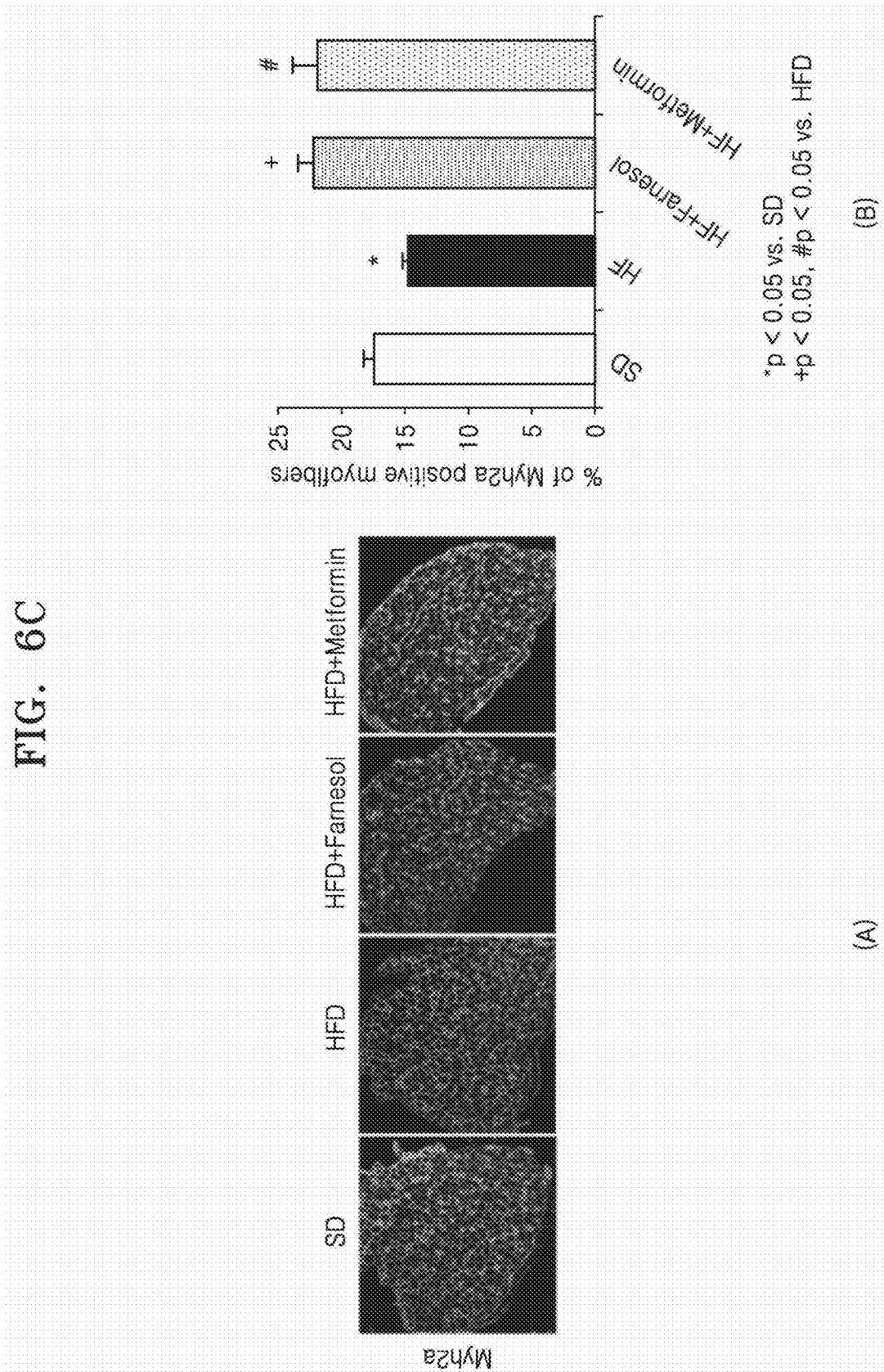
FIG. 6C shows Myh2a immunostaining result of the hind limb muscles of the mice fed with the predetermined diet for 3 months.

FIG. 6C shows Myh2a immunostaining result of the hind limb muscles of the mice fed with the predetermined diet for 3 months. As shown in FIG. 6C, farnesol or metformin treatment significantly increases a percentage of Myh2a-postive muscle fibers, indicating that farnesol increases a percentage of Myh2a-postive muscle fibers by increasing PGC-1α level. In FIG. 6C, SD represents a standard diet as a negative control group, HFD represents a high fat diet, and HFD+Farnesol or HFD-metformin represents farnesol or metformin-added HFD, respectively. In FIG. 6C, A is an image showing immunohistological staining of frozen tissue sections for myh2a using anti-myh2a antibody, and the green color represents oxidative 2a type muscle fibers stained with myh2a, and the red color represents the total muscle cells stained with Laminin, B shows a percentage of the green-colored cells to the total cells, that is, red-colored cells and green-colored cells in A.

Figure 6D:
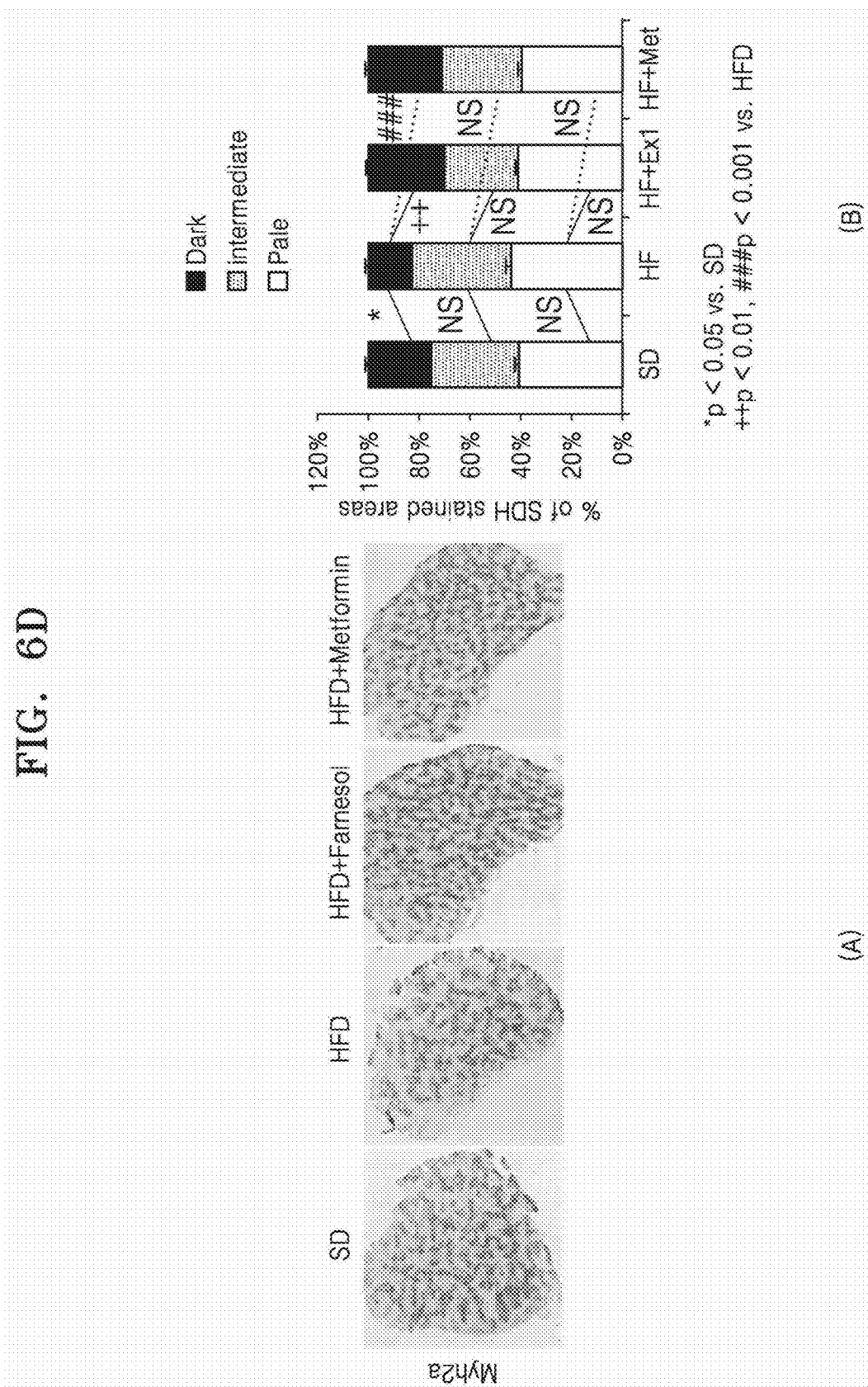
FIG. 6D shows histological staining result of hind limb muscles of the mouse fed with a predetermined diet for 3 months by SDH enzyme activity.

FIG. 6D shows histological staining result of hind limb muscles of the mice fed with a predetermined diet for 3 months by SDH enzyme activity. As shown in FIG. 6D, mitochondrial enzyme activity is decreased by high fat diet, and a percentage of muscle fibers showing increased SDH enzyme activity is increased by addition of farnesol or metformin, compared to the control group, indicating that farnesol or metformin administration activates mitochondrial energy metabolism in muscle fibers. In FIG. 6D, A shows SDH staining result, and B shows a percentage of stained SDH of A, which are classified into three intensities of dark, intermediate, and pale. NS (Non-Significant) stands for not statistically significant, indicating that there is no change by farnesol treatment.

The effects of high fat diet and farnesol and metformin on PGC-1α induction by PARIS-farnesylation are evaluated. To analyze effect of short-term high fat diet, mice are fed with the above conditions for 5 days. Immunoblotting of PGC-1α and PARIS in gastrocnemius muscles of the mice is performed.

Figure 6E:
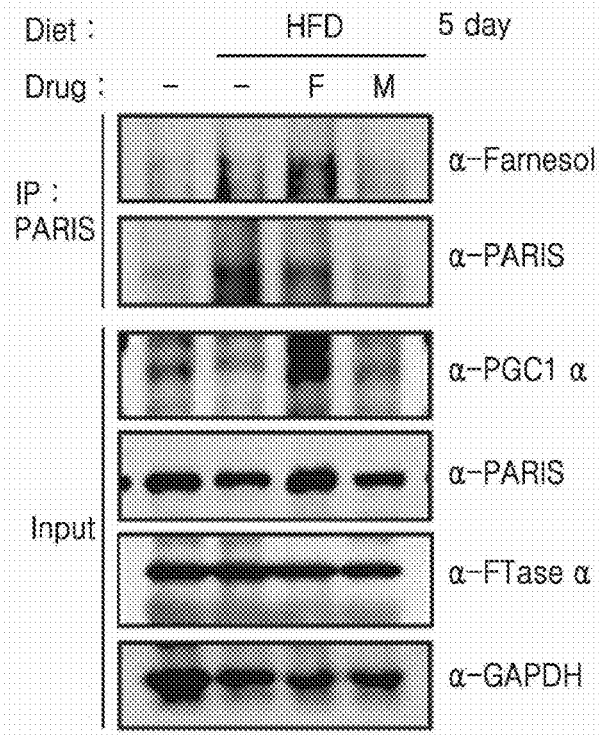
FIG. 6E shows immunoprecipitation analysis for PGC-1α expression and PARIS-farnesylation in the muscles of the mice fed with high fat diet for a short term (5 days)

FIG. 6E shows immunoprecipitation analysis for PGC-1α expression and PARIS-farnesylation in the muscles of the mice fed with high fat diet for a short term (5 days). As shown in the expression levels in Input of FIG. 6E, PGC-1α expression is decreased without changes in the total PARIS level in the muscles of the mice fed with high fat diet for a short term. Immunoprecipitation is performed using PARIS, and as a result, PARIS-farnesylation is decreased by high fat diet. In this regard, PARIS-farnesylation is normalized to the immunoprecipitated PARIS expression level. In contrast, reductions in PARIS-farnesylation and PGC-1α expression are inhibited by farnesol and metformin administrations.

Figure 6F:
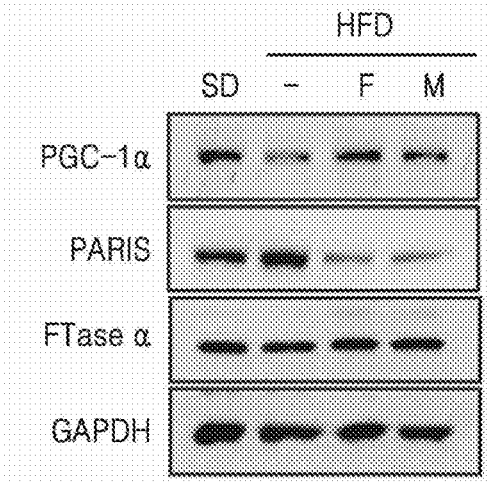
FIG. 6F shows Western blotting result of hind limb muscles of mice fed with a predetermined diet for 3 months.

FIG. 6F shows Western blotting result of hind limb muscles of mice fed with a predetermined diet for 3 months. As shown in FIG. 6F, the increased PARIS level and the decreased PGC-1α expression by high fat diet in the muscle of mouse are inhibited by farnesol and metformin administrations.

Results of Example 7 indicate that PARIS farnesylation may be a target for the treatment of muscle aging and related metabolic diseases.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a disease in a subject in need of such treatment, the treatment comprising administering an effective amount of farnesol, a pharmaceutically acceptable salt thereof, or a solvate thereof to the subject, wherein the disease is sarcopenia, muscle fibrosis, or muscular atrophy.

2. The method of claim 1, comprising administering farnesol to muscle cells.

3. The method of claim 1, wherein the subject is a human 60 years of age or older.

* * * * *